US012746059B2

(12) United States Patent
Okarski et al.

(10) Patent No.: US 12,746,059 B2

(45) Date of Patent: Sep. 29, 2026

(54) SYSTEMS AND METHODS FOR LINEAR SPINES FORMING A SPHERICAL BASKET FOR IMPROVED TISSUE CONTACT AND CURRENT DELIVERY

(71) Applicant: Biosense Webster (Israel) Ltd., Yokneam (IL)

(72) Inventors: Kevin Mark Okarski, Monrovia, CA (US); Keshava Datta, Chino Hills, CA (US); Abubakarr Bah, Irvine, CA (US); Thanh Nguyen, El Monte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 610 days.

(21) Appl. No.: 18/065,748

(22) Filed: Dec. 14, 2022

(65) Prior Publication Data

US 2023/0225787 A1 Jul. 20, 2023

Related U.S. Application Data

(60) Provisional application No. 63/301,102, filed on Jan. 20, 2022.

(51) Int. Cl.

*A61B 18/14* (2006.01)

*A61B 18/00* (2006.01)

(52) U.S. Cl.

CPC .............................. *A61B 18/1492* (2013.01); *A61B 2018/00267* (2013.01); *A61B 2018/1467* (2013.01)

(58) Field of Classification Search

CPC ...... A61B 18/1492; A61B 2018/00267; A61B 2018/1467; A61B 2018/0016; A61B 5/287; A61B 5/6858; A61B 5/6859

See application file for complete search history.

(56) References Cited

U.S. PATENT DOCUMENTS 3,952,747 A 4/1976 Kimmell, Jr.

4,699,147 A 10/1987 Chilson et al.

(Continued)

FOREIGN PATENT DOCUMENTS

CN 105761835 A 7/2016

CN 111248993 A 6/2020

(Continued)

OTHER PUBLICATIONS

Extended European Search Report and Opinion dated Sep. 6, 2023, from corresponding European Application No. 23152472.9.

(Continued)

*Primary Examiner* — Beverly M Flanagan

*Assistant Examiner* — Abigail M Ziegler

(57) ABSTRACT

The disclosed technology includes a medical probe comprising a tubular shaft extending along a longitudinal axis and including a proximal end and a distal end. The medical probe further comprises an expandable basket assembly proximate the distal end of the tubular shaft. The basket assembly comprises a single unitary structure that includes a plurality of linear spines formed from a planar sheet of material and one or more electrodes coupled to each of the spines, each electrode defining a lumen through the electrode so that a spine extends through the lumen of each of the one or more electrodes. The spines converge at a central spine intersection at a distal end of the basket assembly. The central spine intersection includes one or more cutouts that allows for bending of the spines. Each spine comprises a respective end connected to the distal end of the tubular shaft.

20 Claims, 21 Drawing Sheets

(56) References Cited

U.S. PATENT DOCUMENTS 4,940,064 A 7/1990 Desai
5,215,103 A 6/1993 Desai
5,255,679 A 10/1993 Imran
5,293,869 A 3/1994 Edwards et al.
5,309,910 A 5/1994 Edwards et al.
5,313,943 A 5/1994 Houser et al.
5,324,284 A 6/1994 Imran
5,345,936 A 9/1994 Pomeranz et al.
5,365,926 A 11/1994 Desai
5,396,887 A 3/1995 Imran
5,400,783 A 3/1995 Pomeranz et al.
5,411,025 A 5/1995 Webster, Jr.
5,415,166 A 5/1995 Imran
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,681,280 A 10/1997 Rusk et al.
5,718,241 A 2/1998 Ben-Haim et al.
5,722,401 A 3/1998 Pietroski et al.
5,722,403 A 3/1998 McGee et al.
5,725,525 A 3/1998 Kordis
5,730,128 A 3/1998 Pomeranz et al.
5,772,590 A 6/1998 Webster, Jr.
5,782,239 A 7/1998 Webster, Jr.
5,782,899 A 7/1998 Imran
5,823,189 A 10/1998 Kordis
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,944,022 A 8/1999 Nardella et al.
5,968,040 A 10/1999 Swanson et al.
5,983,126 A 11/1999 Wittkampf
6,014,579 A 1/2000 Pomeranz et al.
6,014,590 A 1/2000 Whayne et al.
6,023,638 A 2/2000 Swanson
6,119,030 A 9/2000 Morency
6,198,974 B1 3/2001 Webster, Jr.
6,216,043 B1 4/2001 Swanson et al.
6,216,044 B1 4/2001 Kordis
6,428,537 B1 8/2002 Swanson et al.
6,456,864 B1 9/2002 Swanson et al.
6,484,118 B1 11/2002 Govari
6,574,492 B1 6/2003 Ben-Haim et al.
6,584,345 B2 6/2003 Govari
6,600,948 B2 7/2003 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,837,886 B2 1/2005 Collins et al.
6,866,662 B2 3/2005 Fuimaono et al.
6,892,091 B1 5/2005 Ben-Haim et al.
6,970,730 B2 11/2005 Fuimaono et al.
6,973,340 B2 12/2005 Fuimaono et al.
6,980,858 B2 12/2005 Fuimaono et al.
6,987,995 B2 1/2006 Drysen
7,048,734 B1 5/2006 Fleischman et al.
7,142,903 B2 11/2006 Rodriguez et al.
7,149,563 B2 12/2006 Fuimaono et al.
7,255,695 B2 8/2007 Falwell et al.
7,257,434 B2 8/2007 Fuimaono et al.
7,274,957 B2 9/2007 Drysen
7,377,906 B2 5/2008 Selkee
7,399,299 B2 7/2008 Daniel et al.
7,410,486 B2 8/2008 Fuimaono et al.
7,522,950 B2 4/2009 Fuimaono et al.
7,591,799 B2 9/2009 Selkee
7,593,760 B2 9/2009 Rodriguez et al.
RE41,334 E 5/2010 Beatty et al.
7,720,517 B2 5/2010 Drysen
7,794,473 B2 9/2010 Tessmer et al.
7,846,157 B2 12/2010 Kozel
7,853,302 B2 12/2010 Rodriguez et al.
7,930,018 B2 4/2011 Harlev et al.
8,000,765 B2 8/2011 Rodriguez et al.
8,007,495 B2 8/2011 McDaniel et al.
8,021,327 B2 9/2011 Selkee
8,048,063 B2 11/2011 Aeby et al.
8,103,327 B2 1/2012 Harlev et al.
8,167,845 B2 5/2012 Wang et al.
8,224,416 B2 7/2012 De La Rama et al.
8,235,988 B2 8/2012 Davis et al.
8,275,440 B2 9/2012 Rodriguez et al.
8,295,902 B2 10/2012 Salahieh et al.
8,346,339 B2 1/2013 Kordis et al.
8,357,152 B2 1/2013 Govari et al.
8,435,232 B2 5/2013 Aeby et al.
8,447,377 B2 5/2013 Harlev et al.
8,475,450 B2 7/2013 Govari et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,567,265 B2 10/2013 Aeby et al.
8,712,550 B2 4/2014 Grunewald
8,728,065 B2 5/2014 Fish et al.
8,755,861 B2 6/2014 Harlev et al.
8,825,130 B2 9/2014 Just et al.
8,906,011 B2 12/2014 Gelbart et al.
8,945,120 B2 2/2015 McDaniel et al.
8,979,839 B2 3/2015 De La Rama et al.
9,037,264 B2 5/2015 Just et al.
9,131,980 B2 9/2015 Bloom
9,204,929 B2 12/2015 Solis
9,277,960 B2 3/2016 Weinkam et al.
9,314,208 B1 4/2016 Altmann et al.
9,339,331 B2 5/2016 Tegg et al.
9,486,282 B2 11/2016 Solis
9,554,718 B2 1/2017 Bar-Tal et al.
D782,686 S 3/2017 Werneth et al.
9,585,588 B2 3/2017 Marecki et al.
9,597,036 B2 3/2017 Aeby et al.
9,687,297 B2 6/2017 Just et al.
9,693,733 B2 7/2017 Altmann et al.
9,782,099 B2 10/2017 Williams et al.
9,788,895 B2 10/2017 Solis
9,801,681 B2 10/2017 Laske et al.
9,814,618 B2 11/2017 Nguyen et al.
9,833,161 B2 12/2017 Govari
9,848,795 B2 12/2017 Marecki et al.
9,894,756 B2 2/2018 Weinkam et al.
9,895,073 B2 2/2018 Solis
9,907,609 B2 3/2018 Cao et al.
9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,045,707 B2 8/2018 Govari
10,078,713 B2 9/2018 Auerbach et al.
10,111,623 B2 10/2018 Jung et al.
10,130,420 B2 11/2018 Basu et al.
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.

(56) References Cited

U.S. PATENT DOCUMENTS

| | | | |
|---|---|---|---|
| 10,231,328 | B2 | 3/2019 | Weinkam et al. |
| 10,238,309 | B2 | 3/2019 | Bar-Tal et al. |
| 10,278,590 | B2 | 5/2019 | Salvestro et al. |
| D851,774 | S | 6/2019 | Werneth et al. |
| 10,314,505 | B2 | 6/2019 | Williams et al. |
| 10,314,507 | B2 | 6/2019 | Govari et al. |
| 10,314,648 | B2 | 6/2019 | Ge et al. |
| 10,314,649 | B2 | 6/2019 | Bakos et al. |
| 10,342,608 | B2 | 7/2019 | Wang et al. |
| 10,349,855 | B2 | 7/2019 | Zeidan et al. |
| 10,350,003 | B2 | 7/2019 | Weinkam et al. |
| 10,362,991 | B2 | 7/2019 | Tran et al. |
| 10,375,827 | B2 | 8/2019 | Weinkam et al. |
| 10,376,170 | B2 | 8/2019 | Quinn et al. |
| 10,376,221 | B2 | 8/2019 | Iyun et al. |
| 10,398,348 | B2 | 9/2019 | Osadchy et al. |
| 10,403,053 | B2 | 9/2019 | Katz et al. |
| 10,441,188 | B2 | 10/2019 | Katz et al. |
| 10,470,682 | B2 | 11/2019 | Deno et al. |
| 10,470,714 | B2 | 11/2019 | Altmann et al. |
| 10,482,198 | B2 | 11/2019 | Auerbach et al. |
| 10,492,857 | B2 | 12/2019 | Guggenberger et al. |
| 10,542,620 | B2 | 1/2020 | Weinkam et al. |
| 10,575,743 | B2 | 3/2020 | Basu et al. |
| 10,575,745 | B2 | 3/2020 | Solis |
| 10,582,871 | B2 | 3/2020 | Williams et al. |
| 10,582,894 | B2 | 3/2020 | Ben Zrihem et al. |
| 10,596,346 | B2 | 3/2020 | Aeby et al. |
| 10,602,947 | B2 | 3/2020 | Govari et al. |
| 10,617,467 | B2 | 4/2020 | Viswanathan et al. |
| 10,617,867 | B2 | 4/2020 | Viswanathan et al. |
| 10,660,702 | B2 | 5/2020 | Viswanathan et al. |
| 10,667,753 | B2 | 6/2020 | Werneth et al. |
| 10,674,929 | B2 | 6/2020 | Houben et al. |
| 10,681,805 | B2 | 6/2020 | Weinkam et al. |
| 10,682,181 | B2 | 6/2020 | Cohen et al. |
| 10,687,892 | B2 | 6/2020 | Long et al. |
| 10,688,278 | B2 | 6/2020 | Beeckler et al. |
| 10,702,178 | B2 | 7/2020 | Dahlen et al. |
| 10,716,477 | B2 | 7/2020 | Salvestro et al. |
| 10,758,304 | B2 | 9/2020 | Aujla |
| 10,765,371 | B2 | 9/2020 | Hayam et al. |
| 10,772,566 | B2 | 9/2020 | Aujila |
| 10,799,281 | B2 | 10/2020 | Goertzen et al. |
| 10,842,558 | B2 | 11/2020 | Harlev et al. |
| 10,842,561 | B2 | 11/2020 | Viswanathan et al. |
| 10,863,914 | B2 | 12/2020 | Govari et al. |
| 10,881,376 | B2 | 1/2021 | Shemesh et al. |
| 10,898,139 | B2 | 1/2021 | Guta et al. |
| 10,905,329 | B2 | 2/2021 | Bar-Tal et al. |
| 10,912,484 | B2 | 2/2021 | Ziv-Ari et al. |
| 10,918,306 | B2 | 2/2021 | Govari et al. |
| 10,939,871 | B2 | 3/2021 | Altmann et al. |
| 10,952,795 | B2 | 3/2021 | Cohen et al. |
| 10,973,426 | B2 | 4/2021 | Williams et al. |
| 10,973,461 | B2 | 4/2021 | Baram et al. |
| 10,987,045 | B2 | 4/2021 | Basu et al. |
| 11,006,902 | B1 | 5/2021 | Bonyak et al. |
| 11,040,208 | B1 | 6/2021 | Govari et al. |
| 11,045,628 | B2 | 6/2021 | Beeckler et al. |
| 11,051,877 | B2 | 7/2021 | Sliwa et al. |
| 11,071,585 | B2 | 7/2021 | Zhang et al. |
| 11,109,788 | B2 | 9/2021 | Rottmann et al. |
| 11,116,435 | B2 | 9/2021 | Urman et al. |
| 11,129,574 | B2 | 9/2021 | Cohen et al. |
| 11,160,482 | B2 | 11/2021 | Solis |
| 11,164,371 | B2 | 11/2021 | Yellin et al. |
| 2002/0198522 | A1 | 12/2002 | Kordis et al. |
| 2004/0210121 | A1 | 10/2004 | Fuimaono et al. |
| 2006/0009689 | A1 | 1/2006 | Fuimaono et al. |
| 2006/0009690 | A1 | 1/2006 | Fuimaono et al. |
| 2006/0058813 | A1 | 3/2006 | Teague et al. |
| 2006/0100669 | A1 | 5/2006 | Fuimaono et al. |
| 2007/0093806 | A1 | 4/2007 | Desai et al. |
| 2007/0276212 | A1 | 11/2007 | Fuimaono et al. |
| 2008/0234564 | A1 | 9/2008 | Beatty et al. |
| 2009/0149848 | A1 | 6/2009 | Werneth et al. |
| 2010/0063478 | A1 | 3/2010 | Selkee |
| 2011/0118726 | A1 | 5/2011 | De La Rama et al. |
| 2011/0130648 | A1 | 6/2011 | Beeckler et al. |
| 2011/0160574 | A1 | 6/2011 | Harlev et al. |
| 2011/0190625 | A1 | 8/2011 | Harlev et al. |
| 2011/0245756 | A1 | 10/2011 | Arora et al. |
| 2011/0301597 | A1 | 12/2011 | McDaniel et al. |
| 2012/0271136 | A1 | 10/2012 | Kordis et al. |
| 2012/0271138 | A1 | 10/2012 | Kordis et al. |
| 2012/0271140 | A1 | 10/2012 | Kordis et al. |
| 2013/0090651 | A1 | 4/2013 | Smith |
| 2013/0150693 | A1 | 6/2013 | D'Angelo |
| 2013/0172715 | A1* | 7/2013 | Just ..................... A61B 5/6858 606/41 |
| 2013/0172872 | A1 | 7/2013 | Subramaniam et al. |
| 2013/0172883 | A1 | 7/2013 | Lopes et al. |
| 2013/0178850 | A1 | 7/2013 | Lopes et al. |
| 2013/0190587 | A1 | 7/2013 | Lopes et al. |
| 2013/0296852 | A1 | 11/2013 | Madjarov et al. |
| 2014/0025069 | A1 | 1/2014 | Willard et al. |
| 2014/0052118 | A1 | 2/2014 | Laske et al. |
| 2014/0088588 | A1 | 3/2014 | Jarrard |
| 2014/0180147 | A1 | 6/2014 | Thakur et al. |
| 2014/0180151 | A1 | 6/2014 | Maskara et al. |
| 2014/0180152 | A1 | 6/2014 | Maskara et al. |
| 2014/0257069 | A1 | 9/2014 | Eliason et al. |
| 2014/0276712 | A1 | 9/2014 | Mallin et al. |
| 2014/0276746 | A1 | 9/2014 | Nabutovsky et al. |
| 2014/0288552 | A1 | 9/2014 | Kunis |
| 2014/0309512 | A1 | 10/2014 | Govari et al. |
| 2014/0309513 | A1 | 10/2014 | Fish et al. |
| 2014/0350551 | A1 | 11/2014 | Raatikka et al. |
| 2015/0011991 | A1 | 1/2015 | Buysman et al. |
| 2015/0045863 | A1 | 2/2015 | Litscher et al. |
| 2015/0080693 | A1 | 3/2015 | Solis |
| 2015/0105770 | A1 | 4/2015 | Amit |
| 2015/0119878 | A1 | 4/2015 | Heisel et al. |
| 2015/0133919 | A1 | 5/2015 | McDaniel et al. |
| 2015/0208942 | A1 | 7/2015 | Bar-Tal et al. |
| 2015/0223757 | A1 | 8/2015 | Werneth et al. |
| 2015/0250424 | A1 | 9/2015 | Govari et al. |
| 2015/0270634 | A1 | 9/2015 | Buesseler et al. |
| 2015/0282859 | A1 | 10/2015 | Bencn et al. |
| 2015/0342491 | A1 | 12/2015 | Marecki et al. |
| 2015/0342532 | A1 | 12/2015 | Basu et al. |
| 2015/0351625 | A1 | 12/2015 | Schroth et al. |
| 2015/0366508 | A1 | 12/2015 | Chou et al. |
| 2016/0081746 | A1 | 3/2016 | Solis |
| 2016/0113582 | A1 | 4/2016 | Altmann et al. |
| 2016/0113709 | A1 | 4/2016 | Maor |
| 2016/0183877 | A1 | 6/2016 | Williams et al. |
| 2016/0228023 | A1 | 8/2016 | Govari |
| 2016/0228062 | A1 | 8/2016 | Altmann et al. |
| 2016/0278853 | A1 | 9/2016 | Ogle et al. |
| 2016/0302858 | A1 | 10/2016 | Bencini |
| 2016/0324573 | A1 | 11/2016 | Mickelson et al. |
| 2016/0338770 | A1 | 11/2016 | Bar-Tal et al. |
| 2017/0027638 | A1 | 2/2017 | Solis |
| 2017/0035496 | A1 | 2/2017 | Nagale et al. |
| 2017/0065227 | A1 | 3/2017 | Marrs et al. |
| 2017/0071543 | A1 | 3/2017 | Basu et al. |
| 2017/0071544 | A1 | 3/2017 | Basu et al. |
| 2017/0071665 | A1 | 3/2017 | Solis |
| 2017/0095173 | A1 | 4/2017 | Bar-Tal et al. |
| 2017/0100187 | A1 | 4/2017 | Basu et al. |
| 2017/0143227 | A1 | 5/2017 | Marecki et al. |
| 2017/0156790 | A1 | 6/2017 | Aujla |
| 2017/0164858 | A1 | 6/2017 | Basu |
| 2017/0172442 | A1 | 6/2017 | Govari |
| 2017/0172651 | A1 | 6/2017 | Gross et al. |
| 2017/0185702 | A1 | 6/2017 | Auerbach et al. |
| 2017/0202515 | A1 | 7/2017 | Zrihem et al. |
| 2017/0221262 | A1 | 8/2017 | Laughner et al. |
| 2017/0224958 | A1 | 8/2017 | Cummings et al. |
| 2017/0265812 | A1 | 9/2017 | Williams et al. |
| 2017/0281031 | A1 | 10/2017 | Houben et al. |
| 2017/0281268 | A1 | 10/2017 | Tran et al. |

(56) References Cited

U.S. PATENT DOCUMENTS

| | | | |
|---|---|---|---|
| 2017/0296125 A1 | 10/2017 | Altmann et al. | |
| 2017/0296251 A1 | 10/2017 | Wu et al. | |
| 2017/0319140 A1 | 11/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0000540 A1 | 1/2018 | Ogle et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1* | 3/2018 | Auerbach | A61M 25/0082 |
| 2018/0116595 A1 | 5/2018 | Ruppersberg | |
| 2018/0132749 A1 | 5/2018 | Govari et al. | |
| 2018/0137687 A1 | 5/2018 | Katz et al. | |
| 2018/0160936 A1 | 6/2018 | Govari et al. | |
| 2018/0160978 A1 | 6/2018 | Cohen et al. | |
| 2018/0161577 A1 | 6/2018 | Goedeke et al. | |
| 2018/0168511 A1 | 6/2018 | Hall et al. | |
| 2018/0184982 A1 | 7/2018 | Basu et al. | |
| 2018/0192958 A1 | 7/2018 | Wu | |
| 2018/0192959 A1 | 7/2018 | Mou et al. | |
| 2018/0206792 A1 | 7/2018 | Auerbach et al. | |
| 2018/0228439 A1 | 8/2018 | Wu et al. | |
| 2018/0235692 A1 | 8/2018 | Efimov et al. | |
| 2018/0249959 A1 | 9/2018 | Osypka | |
| 2018/0256109 A1 | 9/2018 | Wu et al. | |
| 2018/0279954 A1 | 10/2018 | Hayam et al. | |
| 2018/0303414 A1 | 10/2018 | Toth et al. | |
| 2018/0303546 A1 | 10/2018 | Buysman et al. | |
| 2018/0310987 A1 | 11/2018 | Altmann et al. | |
| 2018/0311497 A1 | 11/2018 | Viswanathan et al. | |
| 2018/0338722 A1 | 11/2018 | Altmann et al. | |
| 2018/0344188 A1 | 12/2018 | Govari | |
| 2018/0344202 A1 | 12/2018 | Bar-Tal et al. | |
| 2018/0344251 A1 | 12/2018 | Harlev et al. | |
| 2018/0344393 A1 | 12/2018 | Gruba et al. | |
| 2018/0360534 A1 | 12/2018 | Teplitsky et al. | |
| 2018/0365355 A1 | 12/2018 | Auerbach et al. | |
| 2019/0000540 A1 | 1/2019 | Cohen et al. | |
| 2019/0008582 A1 | 1/2019 | Govari et al. | |
| 2019/0015007 A1 | 1/2019 | Rottmann et al. | |
| 2019/0030328 A1 | 1/2019 | Stewart et al. | |
| 2019/0053708 A1 | 2/2019 | Gliner | |
| 2019/0059766 A1 | 2/2019 | Houben et al. | |
| 2019/0069950 A1 | 3/2019 | Viswanathan et al. | |
| 2019/0069954 A1 | 3/2019 | Cohen et al. | |
| 2019/0117111 A1 | 4/2019 | Osadchy et al. | |
| 2019/0117303 A1 | 4/2019 | Claude et al. | |
| 2019/0117315 A1 | 4/2019 | Keyes et al. | |
| 2019/0125338 A1 | 5/2019 | Shelton, IV et al. | |
| 2019/0125437 A1 | 5/2019 | Govari et al. | |
| 2019/0125439 A1 | 5/2019 | Rohl et al. | |
| 2019/0133552 A1 | 5/2019 | Shemesh et al. | |
| 2019/0142293 A1 | 5/2019 | Solis | |
| 2019/0164633 A1 | 5/2019 | Ingel et al. | |
| 2019/0167137 A1 | 6/2019 | Bar-Tal et al. | |
| 2019/0167140 A1 | 6/2019 | Williams et al. | |
| 2019/0188909 A1 | 6/2019 | Yellin et al. | |
| 2019/0201664 A1 | 7/2019 | Govari | |
| 2019/0209089 A1 | 7/2019 | Baram et al. | |
| 2019/0216346 A1 | 7/2019 | Ghodrati et al. | |
| 2019/0216347 A1 | 7/2019 | Ghodrati et al. | |
| 2019/0231421 A1 | 8/2019 | Viswanathan et al. | |
| 2019/0231423 A1 | 8/2019 | Weinkam et al. | |
| 2019/0239811 A1 | 8/2019 | Just et al. | |
| 2019/0246935 A1 | 8/2019 | Govari et al. | |
| 2019/0298442 A1 | 10/2019 | Ogata et al. | |
| 2019/0314083 A1 | 10/2019 | Herrera et al. | |
| 2019/0328260 A1 | 10/2019 | Zeidan et al. | |
| 2019/0336210 A1 | 11/2019 | Beeckler et al. | |
| 2019/0343580 A1 | 11/2019 | Nguyen et al. | |
| 2019/0350567 A1 | 11/2019 | Cummins et al. | |
| 2019/0350647 A1 | 11/2019 | Ramberg et al. | |
| 2020/0000518 A1 | 1/2020 | Kiernan et al. | |
| 2020/0008705 A1 | 1/2020 | Ziv-Ari et al. | |
| 2020/0008869 A1 | 1/2020 | Byrd | |
| 2020/0009378 A1 | 1/2020 | Stewart et al. | |
| 2020/0015876 A1 | 1/2020 | Chou et al. | |
| 2020/0015890 A1 | 1/2020 | To et al. | |
| 2020/0022653 A1 | 1/2020 | Moisa | |
| 2020/0029845 A1 | 1/2020 | Baram et al. | |
| 2020/0046421 A1 | 2/2020 | Govari | |
| 2020/0046423 A1 | 2/2020 | Viswanathan et al. | |
| 2020/0060569 A1 | 2/2020 | Tegg | |
| 2020/0077959 A1 | 3/2020 | Altmann et al. | |
| 2020/0093539 A1 | 3/2020 | Long et al. | |
| 2020/0129089 A1 | 4/2020 | Gliner et al. | |
| 2020/0129125 A1 | 4/2020 | Govari et al. | |
| 2020/0129128 A1 | 4/2020 | Gliner et al. | |
| 2020/0179650 A1 | 6/2020 | Beeckler et al. | |
| 2020/0196896 A1 | 6/2020 | Solis | |
| 2020/0197082 A1 | 6/2020 | Daniel et al. | |
| 2020/0205689 A1 | 7/2020 | Squires et al. | |
| 2020/0205690 A1 | 7/2020 | Williams et al. | |
| 2020/0205737 A1 | 7/2020 | Beeckler | |
| 2020/0205876 A1 | 7/2020 | Govari | |
| 2020/0205892 A1 | 7/2020 | Viswanathan et al. | |
| 2020/0206461 A1 | 7/2020 | Govari et al. | |
| 2020/0206498 A1 | 7/2020 | Arora et al. | |
| 2020/0289197 A1 | 9/2020 | Viswanathan et al. | |
| 2020/0297234 A1 | 9/2020 | Houben et al. | |
| 2020/0297281 A1 | 9/2020 | Basu et al. | |
| 2020/0305726 A1 | 10/2020 | Salvestro et al. | |
| 2020/0305946 A1 | 10/2020 | Desimone et al. | |
| 2020/0375657 A1 | 12/2020 | Olson et al. | |
| 2020/0397328 A1 | 12/2020 | Altmann et al. | |
| 2020/0398048 A1 | 12/2020 | Krimsky et al. | |
| 2021/0015549 A1 | 1/2021 | Haghighi-Mood et al. | |
| 2021/0022684 A1 | 1/2021 | Govari et al. | |
| 2021/0045805 A1 | 2/2021 | Govari et al. | |
| 2021/0059549 A1 | 3/2021 | Urman et al. | |
| 2021/0059550 A1 | 3/2021 | Urman et al. | |
| 2021/0059608 A1 | 3/2021 | Beeckler et al. | |
| 2021/0059743 A1 | 3/2021 | Govari | |
| 2021/0059747 A1 | 3/2021 | Krans et al. | |
| 2021/0077184 A1 | 3/2021 | Basu et al. | |
| 2021/0082157 A1 | 3/2021 | Rosenberg et al. | |
| 2021/0085200 A1 | 3/2021 | Auerbach et al. | |
| 2021/0085204 A1 | 3/2021 | Auerbach et al. | |
| 2021/0085215 A1 | 3/2021 | Auerbach et al. | |
| 2021/0085387 A1 | 3/2021 | Amit et al. | |
| 2021/0093292 A1 | 4/2021 | Baram et al. | |
| 2021/0093294 A1 | 4/2021 | Shemesh et al. | |
| 2021/0093374 A1 | 4/2021 | Govari et al. | |
| 2021/0093376 A1 | 4/2021 | Harlev et al. | |
| 2021/0093377 A1 | 4/2021 | Herrera et al. | |
| 2021/0100612 A1 | 4/2021 | Baron et al. | |
| 2021/0113822 A1 | 4/2021 | Beeckler et al. | |
| 2021/0127999 A1 | 5/2021 | Govari et al. | |
| 2021/0128010 A1 | 5/2021 | Govari et al. | |
| 2021/0133516 A1 | 5/2021 | Govari et al. | |
| 2021/0145282 A1 | 5/2021 | Bar-Tal et al. | |
| 2021/0161582 A1 | 6/2021 | Byrd et al. | |
| 2021/0161592 A1 | 6/2021 | Altmann et al. | |
| 2021/0162210 A1 | 6/2021 | Altmann et al. | |
| 2021/0169421 A1 | 6/2021 | Govari | |
| 2021/0169550 A1 | 6/2021 | Govari et al. | |
| 2021/0169567 A1 | 6/2021 | Govari et al. | |
| 2021/0169568 A1 | 6/2021 | Govari et al. | |
| 2021/0177294 A1 | 6/2021 | Gliner et al. | |
| 2021/0177356 A1 | 6/2021 | Gliner et al. | |
| 2021/0177503 A1 | 6/2021 | Altmann et al. | |
| 2021/0178166 A1 | 6/2021 | Govari et al. | |
| 2021/0186363 A1 | 6/2021 | Gliner et al. | |
| 2021/0186604 A1 | 6/2021 | Altmann et al. | |
| 2021/0187241 A1 | 6/2021 | Govari et al. | |
| 2021/0187254 A1 | 6/2021 | Beeckler et al. | |
| 2021/0196372 A1 | 7/2021 | Altmann et al. | |
| 2021/0196394 A1 | 7/2021 | Govari et al. | |
| 2021/0212591 A1 | 7/2021 | Govari et al. | |
| 2021/0219904 A1 | 7/2021 | Yarnitsky et al. | |
| 2021/0236815 A1 | 8/2021 | Waldstreicher et al. | |
| 2021/0278936 A1 | 9/2021 | Katz et al. | |

(56) References Cited

U.S. PATENT DOCUMENTS

| | | | |
|---|---|---|---|
| 2021/0282659 A1 | 9/2021 | Govari et al. | |
| 2021/0307815 A1 | 10/2021 | Govari et al. | |
| 2021/0308424 A1 | 10/2021 | Beeckler et al. | |
| 2021/0338319 A1 | 11/2021 | Govari et al. | |
| 2021/0369339 A1 | 12/2021 | Salazar et al. | |
| 2022/0071695 A1 | 3/2022 | Beeckler et al. | |
| 2022/0071696 A1 | 3/2022 | Govari et al. | |
| 2022/0110679 A1 | 4/2022 | Wang et al. | |
| 2022/0304745 A1 | 9/2022 | Olson | |
| 2022/0387051 A1 | 12/2022 | Girdhar et al. | |
| 2023/0000550 A1 | 1/2023 | Nedved et al. | |
| 2023/0130692 A1* | 4/2023 | Wang ................. | A61B 18/1492 606/41 |
| 2023/0225790 A1 | 7/2023 | Okarski | |
| 2023/0346455 A1 | 11/2023 | Beeckler et al. | |
| 2023/0346459 A1 | 11/2023 | Beeckler et al. | |
| 2023/0346462 A1 | 11/2023 | Beeckler et al. | |
| 2023/0346464 A1 | 11/2023 | Beeckler et al. | |
| 2024/0216045 A1 | 7/2024 | Keyes | |
| 2025/0057589 A1 | 2/2025 | Sandquist et al. | |

FOREIGN PATENT DOCUMENTS

| | | | |
|---|---|---|---|
| CN | 111248996 | A | 6/2020 |
| EP | 0668740 | A1 | 8/1995 |
| EP | 0644738 | B1 | 3/2000 |
| EP | 0727183 | B1 | 11/2002 |
| EP | 0727184 | B1 | 12/2002 |
| EP | 2201905 | A1 | 6/2010 |
| EP | 2783651 | A1 | 10/2014 |
| EP | 2699151 | B1 | 11/2015 |
| EP | 2699152 | B1 | 11/2015 |
| EP | 2699153 | B1 | 12/2015 |
| EP | 2498706 | B1 | 4/2016 |
| EP | 2578173 | B1 | 6/2017 |
| EP | 3181082 | A1 | 6/2017 |
| EP | 3238645 | A1 | 11/2017 |
| EP | 2884931 | B1 | 1/2018 |
| EP | 3315086 | A1 | 5/2018 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3791816 | A2 | 3/2021 |
| EP | 3972510 | A1 | 3/2022 |
| EP | 4115834 | A1 | 1/2023 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020194216 | A1 | 10/2020 |
| WO | 2020206328 | A1 | 10/2020 |
| WO | 2021126980 | A1 | 6/2021 |
| WO | 2022001908 | A1 | 1/2022 |

OTHER PUBLICATIONS

Extended European Search Report dated Feb. 2, 2023, from Corresponding European Application No. 22194819.3, 8 pages.

Extended European Search Report and Opinion dated Jun. 1, 2023, from corresponding European Application No. 23152493.5.

Extended European Search Report and Opinion dated Jun. 7, 2023, from corresponding European Application No. 23152399.4.

Extended European Search Report and Opinion dated Jun. 12, 2023, from corresponding European Application No. 23152448.9.

Extended European Search Report dated Jun. 13, 2023, from Corresponding European Application No. 23152458.8, 12 pages.

Extended European Search Report & Search Opinion dated Sep. 19, 2023, from corresponding European Application No. 23170325.7.

Extended European Search Report & Search Opinion dated Sep. 21, 2023, from corresponding European Application No. 23170230.9.

Extended European Search Report & Search Opinion dated Sep. 21, 2023, from corresponding European Application No. 23170409.9.

Extended European Search Report & Search Opinion dated Jan. 2, 2024, from corresponding European Application No. 23170297.8.

* cited by examiner

SYSTEMS AND METHODS FOR LINEAR SPINES FORMING A SPHERICAL BASKET FOR IMPROVED TISSUE CONTACT AND CURRENT DELIVERY

CROSS REFERENCE TO RELATED APPLICATIONS

This application claims the benefit of priority under 35 U.S.C. § 119 to prior filed U.S. Provisional Patent Application No. 63/301,102, filed on Jan. 20, 2022, the entire contents of which is hereby incorporated by reference as if set forth in full herein.

FIELD

The present invention relates generally to medical devices, and in particular catheters with electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that generally reduces thermal risks associated with RF ablation but may present tissue damage due to the very low temperature nature of such devices. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached in the appendix to priority application U.S. 63/301,102.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved basket assembly that can help to reduce the time required for manufacturing the basket assembly and alternative catheter geometries in general.

SUMMARY

Various embodiments of a medical probe and related methods are described and illustrated. The medical probe may include a tubular shaft including a proximal end and a distal end. The tubular shaft can extend along a longitudinal axis. The medical probe can include an expandable basket assembly proximate the distal end of the tubular shaft. The basket assembly can include a single unitary structure that includes a plurality of linear spines formed from a planar sheet of material. The spines can converge at a central spine intersection. The central spine intersection can have one or more cutouts that allows for bending of the spines. Each spine can have a respective end connected to the distal end of the tubular shaft. The central spine intersection can be positioned on the longitudinal axis at a distal end of the basket assembly. The expandable basket assembly can include one or more electrodes coupled to each of the spines. Each electrode can define a lumen through the electrode so that a spine extends through the lumen of each of the one or more electrodes.

The disclosed technology can include a spine basket member comprising a plurality of spines extending radially from a central axis; and a cut-out defining a first open area of empty space proximate the central axis. The first open area of empty space can approximate a first virtual circle including a first diameter from the central axis. The cut-out can extend into each of the plurality of spines for a first length to define an open slot in each of the plurality of spines. Each slot can be contiguous to a circumference of a second virtual circle greater than the first virtual circle.

The disclosed technology can include an example method of constructing a medical probe. The method can include cutting a planar sheet of material to form a plurality of linear spines including a central spine intersection; cutting a discrete cutout at the central spine intersection; inserting each spine into a lumen of at least one electrode; and fitting ends of the plurality of linear spines to a tubular shaft sized to traverse vasculature such that the central spine intersection is positioned at a distal end of the medical probe and respective spines are movable from a tubular configuration to a bowed configuration.

DETAILED DESCRIPTION

Figure 1:
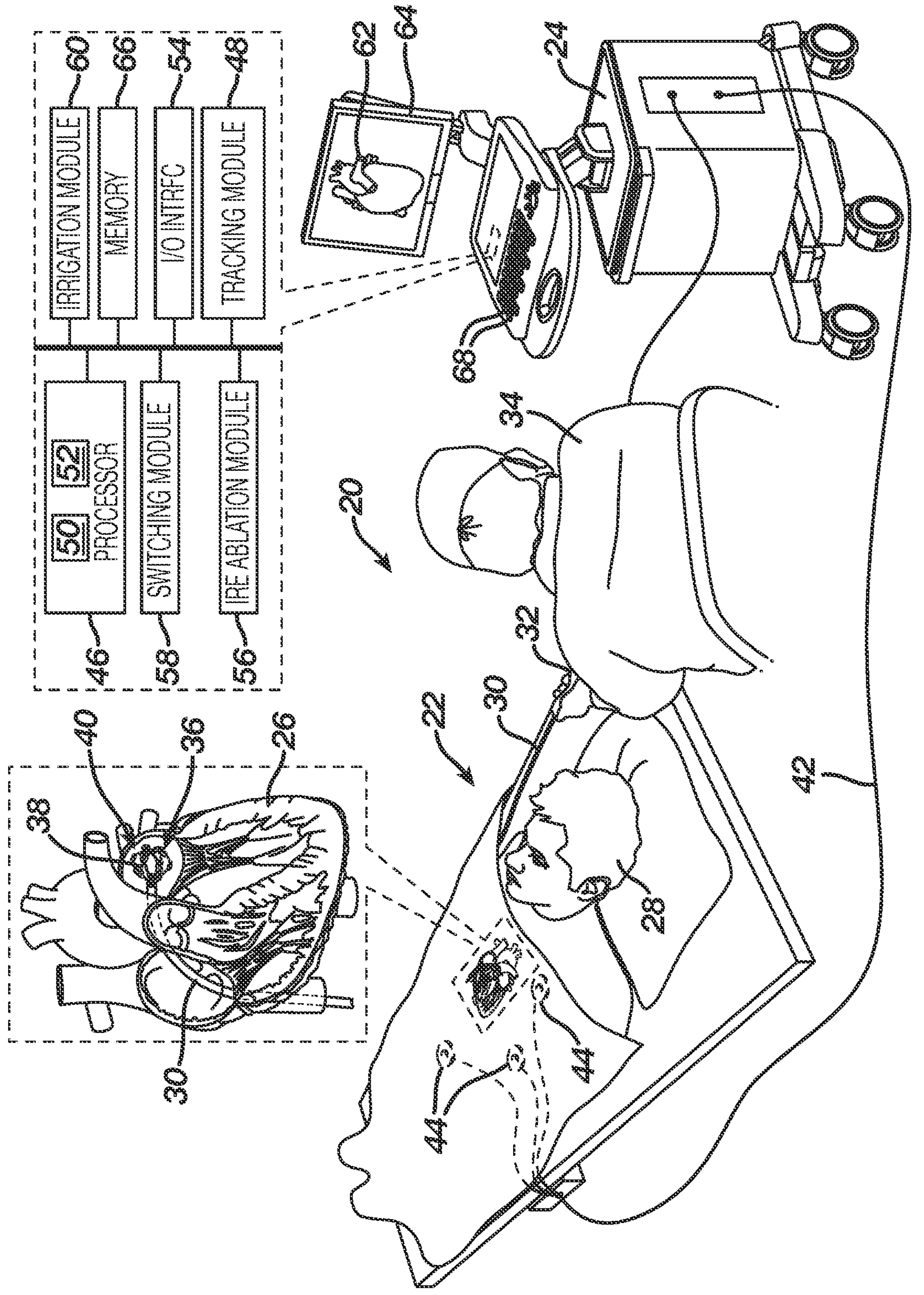
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%.

As used herein, the terms "patient," "host," "user," and "subject" refer to any human or animal subject and are not intended to limit the systems or methods to human use, although use of the subject invention in a human patient represents a preferred embodiment. In addition, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode including a high current density and high electric flux density is positioned at a treatment site, and a second electrode including comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the appendix to priority application U.S. 63/301,102.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated herein by reference and attached in the appendix to priority application U.S. 63/301,102.

To deliver pulsed field ablation (PFA) in an IRE (irreversible electroporation) procedure, electrodes should contact the tissue being ablated with a sufficiently large surface area. As described hereinbelow, the medical probe includes a tubular shaft including proximal and distal ends, and a basket assembly at the distal end of the tubular shaft. The basket assembly includes a single unitary structure. The unitary structure can include a plurality of linear spines formed from a planar sheet of material and one or more electrodes coupled to each of the spines. The plurality of linear spines can converge at a central spine intersection including one or more cutouts. The cutouts can allow for bending of each spine such that the spines form an approximately spherical or oblate-spheroid basket assembly. It is noted that the cutouts (in various configurations described and illustrated in the specification) allows the basket to be compressed into a much smaller form factor when undeployed (or undergoing a retraction into a delivery sheath) without buckling or plastic deformation.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the tubular shaft. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 approximate a distal end 36 of the medical probe 22. Basket assembly 38 can include a plurality of electrodes 40 affixed to a plurality of spines 214, as described in the description referencing FIGS. 2A and 2B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 engages cardiac tissue, the medical professional 34 can activate the medical probe 22 such that electrical pulses are delivered by the electrodes 40 to perform the IRE ablation.

Figure 3A:
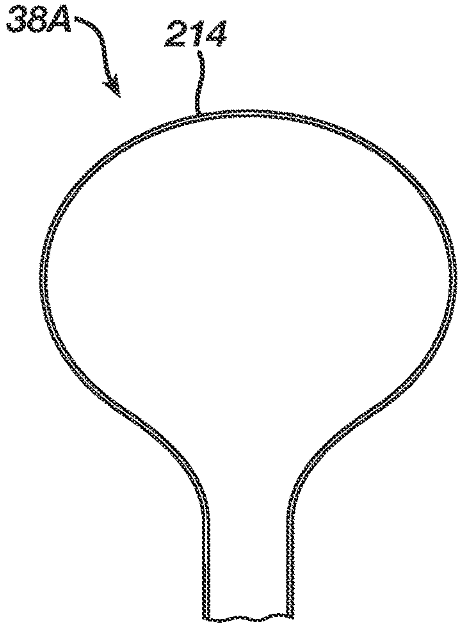
FIGS. 3A and 3B are schematic pictorial illustrations showing a profile outline of a basket assembly of a given medical device, in accordance with embodiments of the present invention.
Figure 3B:
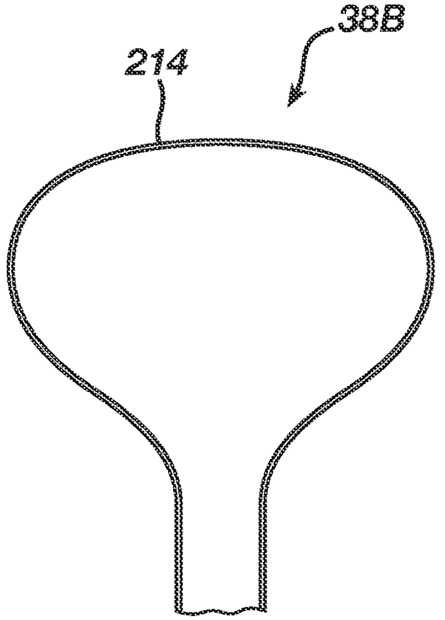
Figure 4:
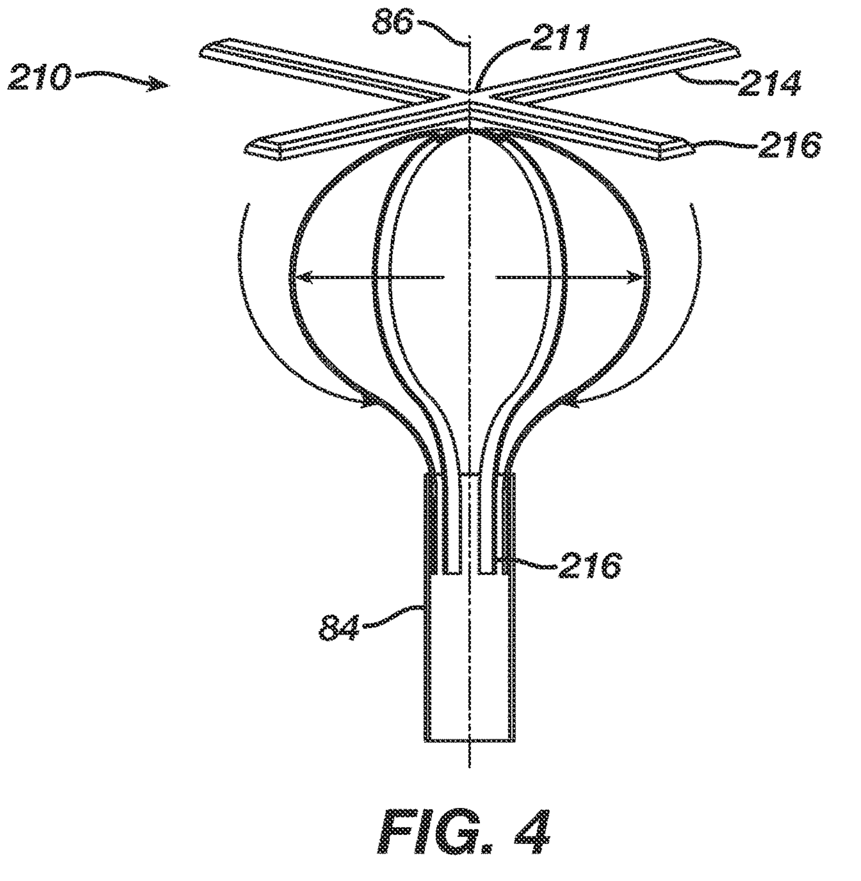
FIG. 4 is a schematic pictorial illustration showing a side view of a plurality of linear spines forming a basket assembly, in accordance with an embodiment of the present invention.

The medical probe 22 can include a guide sheath and a therapeutic catheter, wherein the guide sheath includes the flexible insertion tube 30 and the handle 32 and the therapeutic catheter includes the basket assembly 38, electrodes 40, and a tubular shaft 84 (see FIGS. 2 through 4). The therapeutic catheter is translated through the guide sheath so that the basket assembly 38 is positioned in the heart 26. The distal end 36 of the medical probe 22 corresponds to a distal end of the guide sheath when the basket assembly 38 is contained within the flexible insertion tube 30, and the distal end 36 of the medical probe 22 corresponds to a distal end of the basket assembly 38 when the basket assembly 38 is extended from the distal end of the guide sheath. The medical probe 22 can be alternatively configured to include a second handle on the therapeutic catheter and other features as understood by a person skilled in the pertinent art.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses including peak power in the range of tens of kilowatts. In some examples, the electrodes 40 are configured to deliver electrical pulses including a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

Figure 2A:
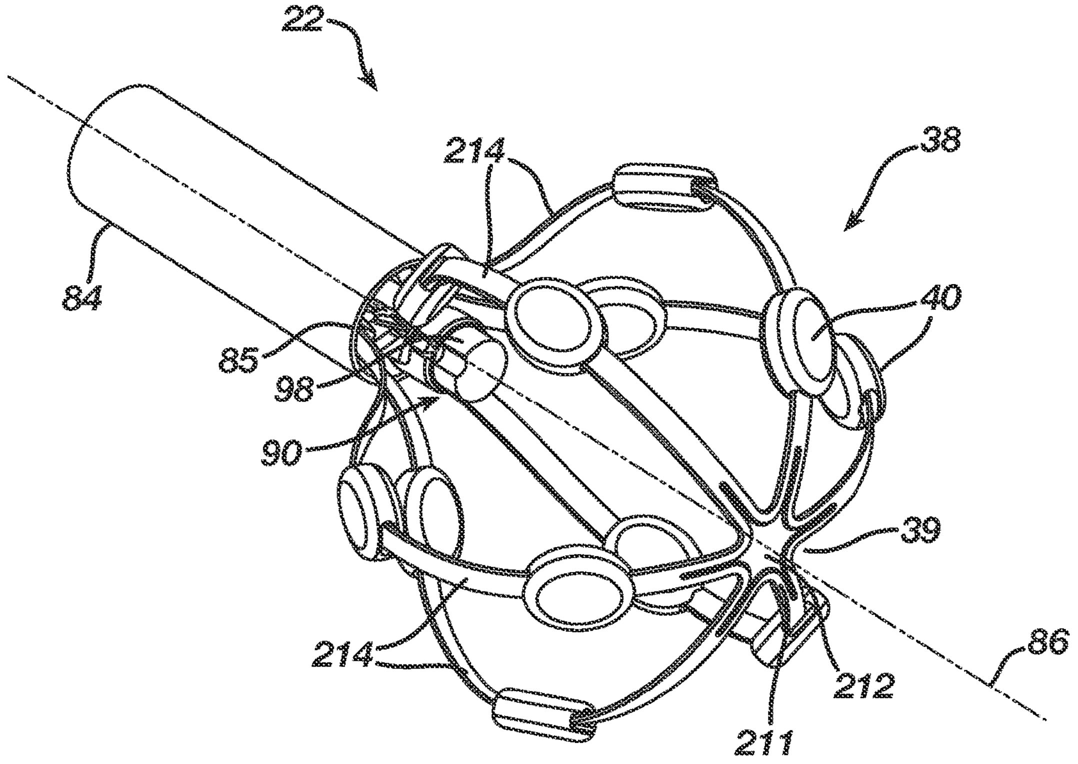
FIG. 2A is a schematic pictorial illustration showing a perspective view of a medical probe in an expanded form, in accordance with an embodiment of the present invention.
Figure 2B:
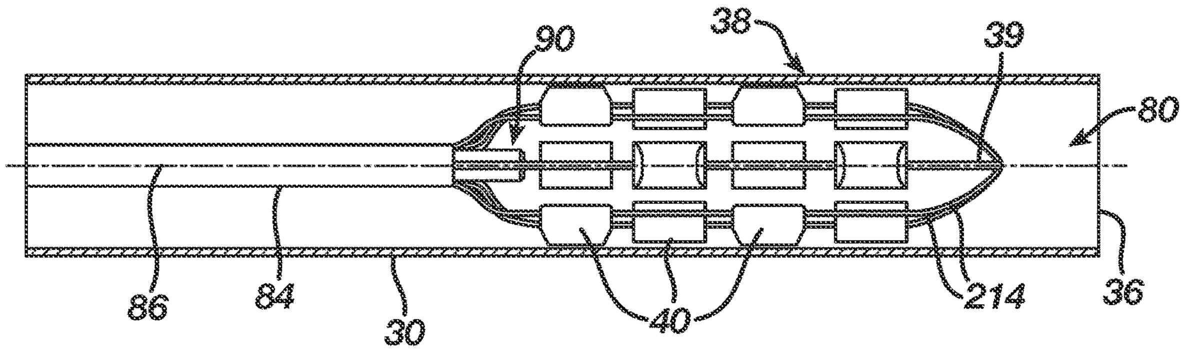
FIG. 2B is a schematic pictorial illustration showing a side view of a medical probe in a collapsed form, in accordance with embodiments of the present invention.
Figure 2C:
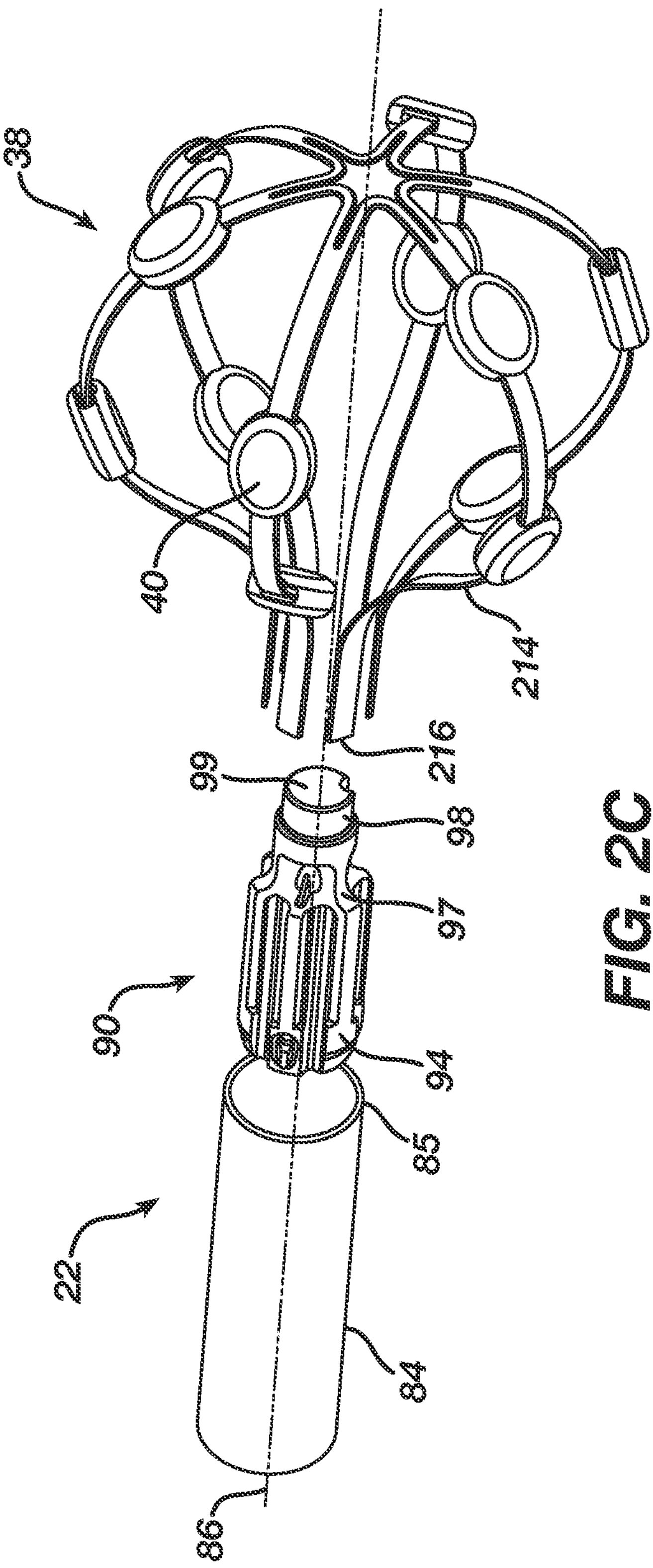
FIG. 2C is a schematic pictorial illustration showing an exploded side view of a medical probe, in accordance with an embodiment of the present invention.

In order to dissipate the heat and to improve the efficiency of the ablation process, system 20 supplies irrigation fluid (e.g., a saline solution) to distal end 36 and to the electrodes 40 via a channel (not shown) in tubular shaft 84 (see FIGS. 2A through 2C). Additionally, or alternatively, irrigation fluid can be supplied through the flexible insertion tube 30. Control console 24 includes an irrigation module 60 to monitor and control irrigation parameters, such as the pressure and the temperature of the irrigation fluid. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

FIG. 2A is a schematic pictorial illustration showing a perspective view of a medical probe 22 including a basket assembly 38 in an expanded form when unconstrained, such as by being advanced out of an insertion tube lumen 80 at a distal end 36 of an insertion tube 30. The medical probe 22 illustrated in FIG. 2A lacks the guide sheath illustrated in FIG. 1. FIG. 2B shows the basket assembly in a collapsed form within insertion tube 30 of the guide sheath. In the expanded form (FIG. 2A), spines 214 bow radially outwardly and in the collapsed form (FIG. 2B) the spines are arranged generally along a longitudinal axis 86 of insertion tube 30.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing basket assembly 38 to exit insertion tube 30 and transition to the expanded form. Spines 214 may have elliptical (e.g., circular) or rectangular (that may appear to be flat) cross-sections, and include a flexible, resilient material (e.g., a shape-memory alloy such as nickel-titanium, also known as Nitinol) forming a strut as will be described in greater detail herein.

As shown in FIG. 2A, the plurality of flexible linear spines 214 converge at a central spine intersection 211. In some examples central spine intersection 211 can include one or more cutouts 212 that allow for bending of the spines 214 when each spine respective attachment end 216 is connected to the spine retention hub 90, described in more detail below.

In embodiments described herein, one or more electrodes 40 positioned on spines 114 of basket assembly 38 can be configured to deliver ablation energy (RF and/or IRE) to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the one or more electrodes 40 face outwardly from basket assembly 38 such that the one or more electrodes 40 deliver a greater amount of electrical energy outwardly away from the basket assembly 38 (i.e., toward the heart 26 tissue) than inwardly.

Examples of materials ideally suited for forming electrodes 40 include gold, platinum and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Basket assembly 38 has a distal end 39. The medical probe 22 can include a spine retention hub 90 that extends longitudinally from a distal end of tubular shaft 84 towards distal end 39 of basket assembly 38. As described supra, control console 24 includes irrigation module 60 that delivers irrigation fluid to basket assembly 38 through tubular shaft 84.

Turning to FIG. 2C, basket assembly 38 includes a single unitary structure that includes a plurality of linear spines 214 formed from a planar sheet of material 210 (shown more clearly in FIGS. 3 and 4A). The spine retention hub 90 can be inserted into the tubular shaft 84 and attached to the tubular shaft 84. Spine retention hub 90 can include a cylindrical member 94 including a plurality of relief lands 96, multiple irrigation openings 98, and at least one spine retention hub electrode 99, or some combination thereof. Relief lands 96 can be disposed on the outer surface of cylindrical member 94 and configured to allow a portion of each spine 214, such as each spine attachment end 216, to be fitted into a respective relief land 96. The attachment end 216 can be a generally linear end of the spine 214. The attachment end 216 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly is deployed.

As described supra, control console 24 includes irrigation module 60 that delivers irrigation fluid to distal end 36. The multiple irrigation openings 98 can be angled to spray or otherwise disperse of the irrigation fluid to either a given electrode 40 or to tissue in heart 26. Since electrodes 40 do not include irrigation openings that deliver irrigation fluid, the configuration described hereinabove enables heat to be transferred from the tissue (i.e., during an ablation procedure) to the portion of the electrodes on the inner side of the spines 214, and the electrodes 40 can be cooled by aiming the irrigation fluid, via irrigation openings 98, at the portion of the electrodes 40 on the inner side of the spines 214. Spine retention hub electrode 99 disposed at a distal end of retention hub 90 can be used in combination with electrodes 40 on the spines 214, or alternatively, can be used independently from electrodes 40 for reference mapping or ablation.

FIGS. 3A and 3B are schematic pictorial illustrations showing a profile outline of a basket assembly 38A, 38B such that when the basket assembly is deployed the spines define a three-dimensional shape including the profile. The basket assembly can be approximately spheroid including an approximately circular profile as shown in FIG. 3A. The basket assembly can have an approximately oblate-spheroid shape including an approximately elliptical profile as shown in FIG. 3B. Although not every variation of shape is shown or described herein, one skilled in the art will appreciate that spines 214 can be further configured to form other various shapes as would be suitable for the particular application.

By including spines 214 configured to form various shapes when in the expanded form, basket assembly 38 can be configured to position the various electrodes 40 attached to spines 214 at various locations, with each location being nearer or farther from the distal end of tubular shaft 84. For example, electrode 40 attached to spine 214 illustrated in FIG. 3A near the middle of spine 214 would be farther from the distal end of tubular shaft 84 than spine 214 illustrated in FIG. 3B when basket assembly 38 is in the expanded form. In addition, each spine 214 may have an elliptical (e.g., circular) or rectangular (that may appear to be flat) cross-section, and include a flexible, resilient material (e.g., a shape-memory alloy such as nickel-titanium (also known as Nitinol), cobalt chromium, or any other suitable material).

Figure 5A:
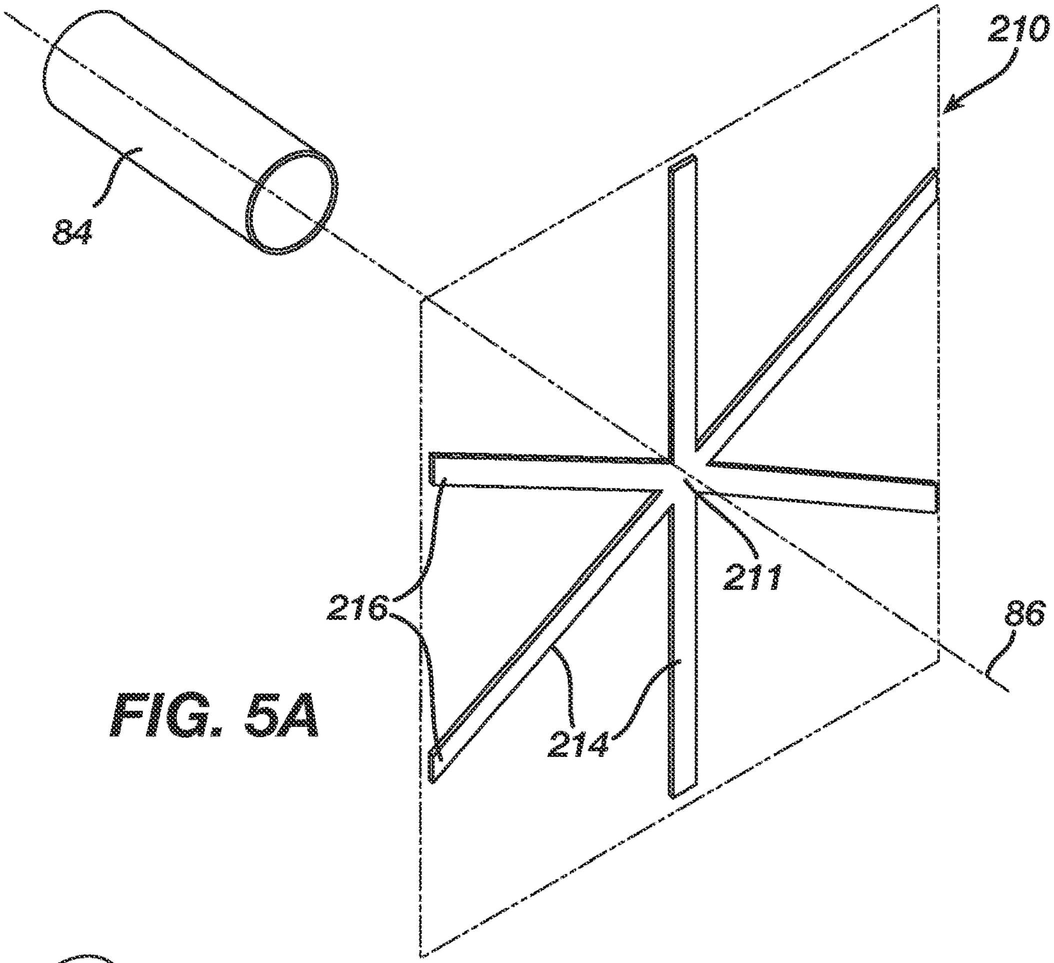
FIGS. 5A and 5B are schematic pictorial illustrations of a method of forming a basket assembly, in accordance with an embodiment of the present invention.
Figure 5B:
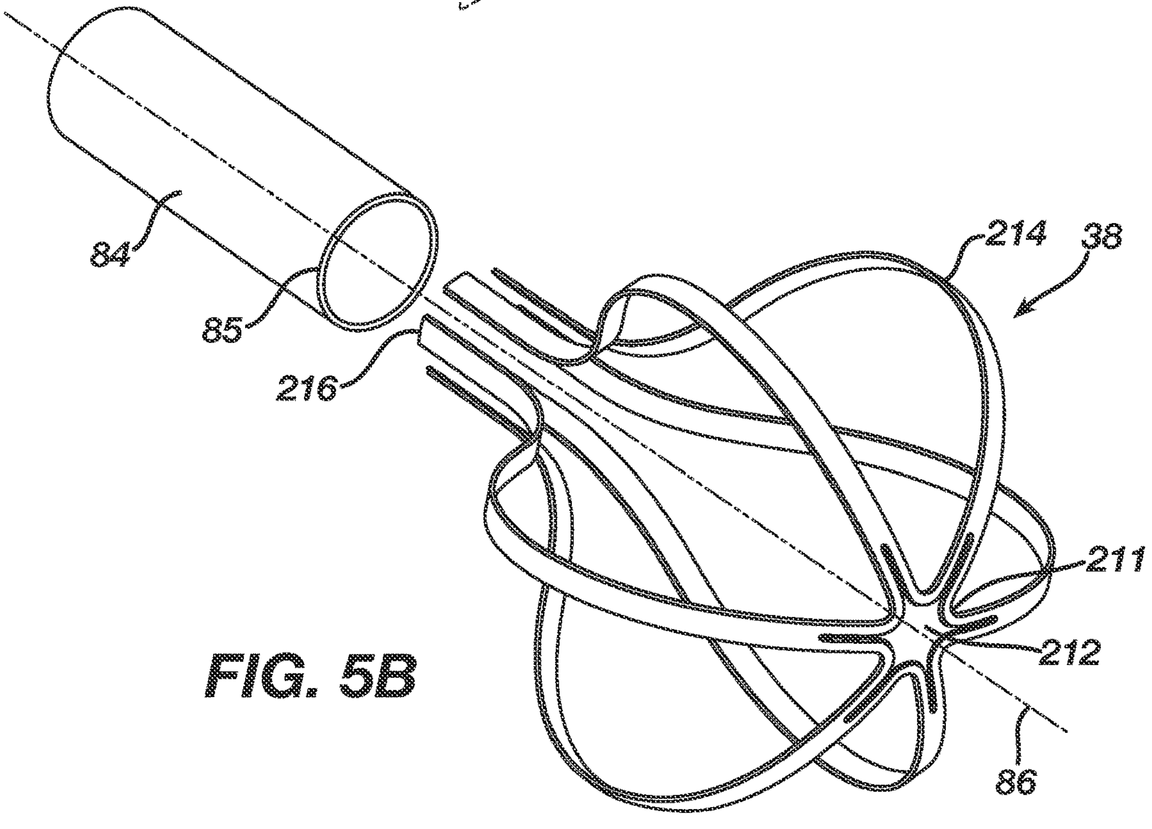

FIGS. 4, 5A and 5B are schematic pictorial illustrations showing views of spines 214 forming basket assembly 38. FIG. 4 provides one example of how planar sheet of material 210 may be assembled together with tubular shaft 84 whereby each spine 214 bends or curves when respective attachment ends 216 are connect to spine retention hub 90. As shown in FIG. 5A, the spines 214 can be formed from a single sheet of planar material 210 to form a generally star shape. In other words, spines 214 can be formed from the single sheet of planar material such that the spines 214 converge toward a central intersection 211. The intersection 211 can be a solid piece of material (as shown in FIG. 5A) or include one or more cutouts 212 (as shown in FIG. 5B). Basket assembly 38 can include a number of spines 214 ranging from about four to about ten spines from a single sheet of planar material 210.

Figure 5C:
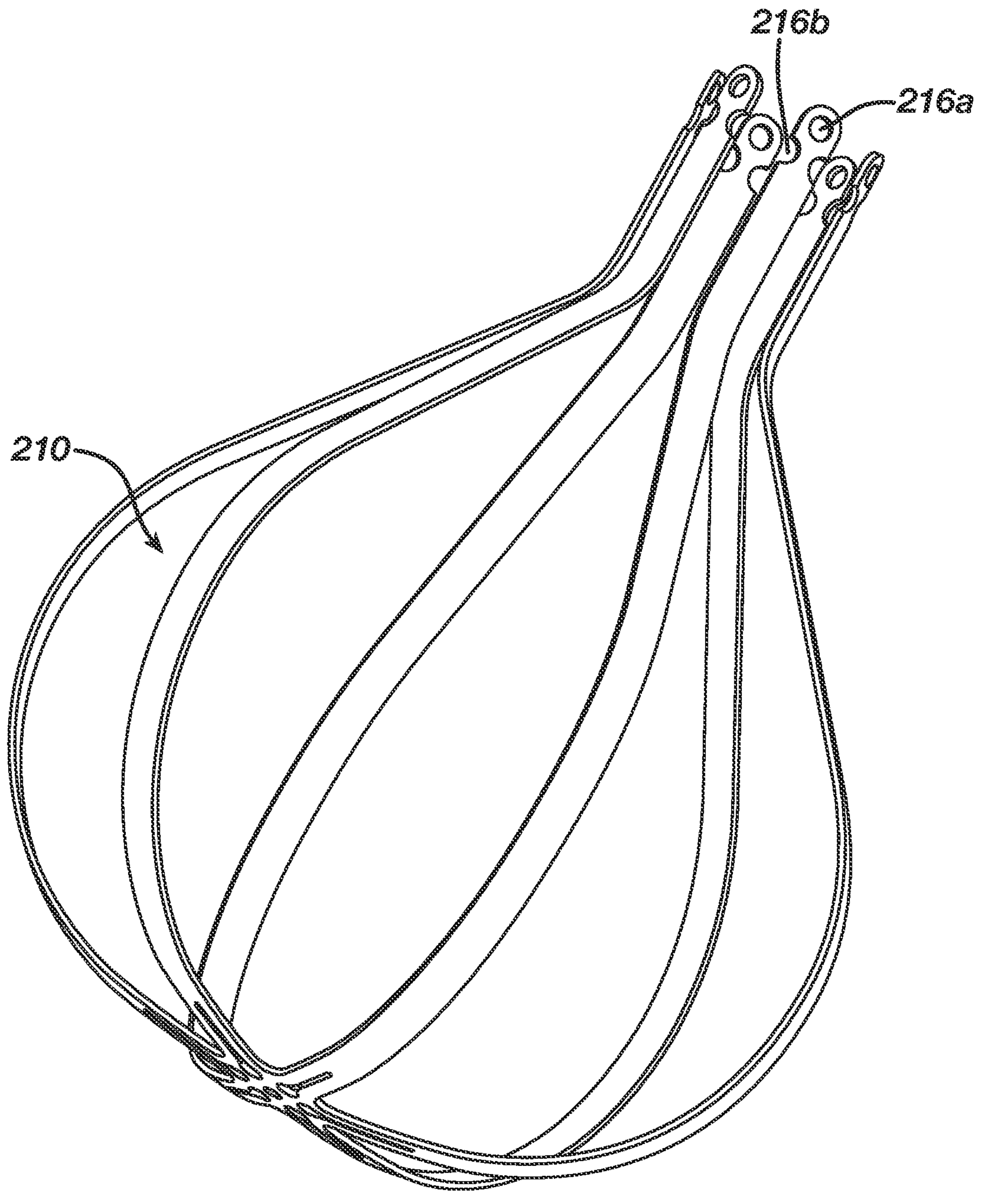
FIG. 5C illustrates an embodiment where the proximal end of each spine is provided with a hole and reference notches to ensure correct alignment and retention of the spine to the irrigation tube, in accordance with an embodiment of the present invention.
Figure 5D:
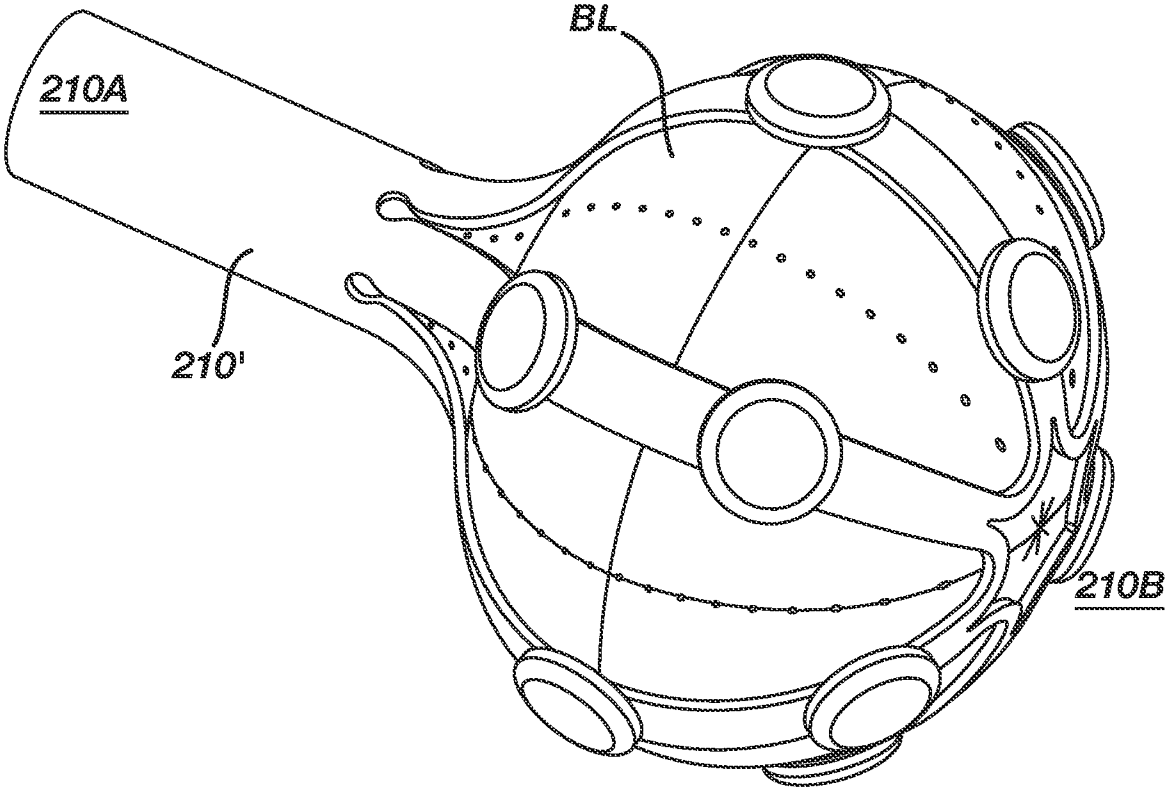
FIG. 5D illustrates an embodiment that relies on a balloon to expand the spine assembly, in accordance with an embodiment of the present invention.
Figure 5E:
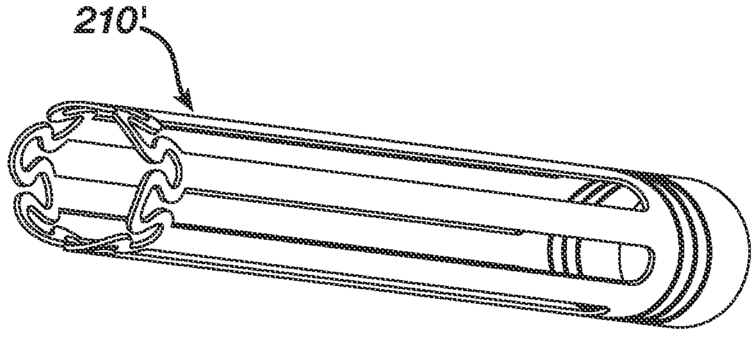
FIG. 5E illustrates a spine assembly formed by cutting a cylindrical tube stock with a laser, in accordance with an embodiment of the present invention.
Figure 5F:
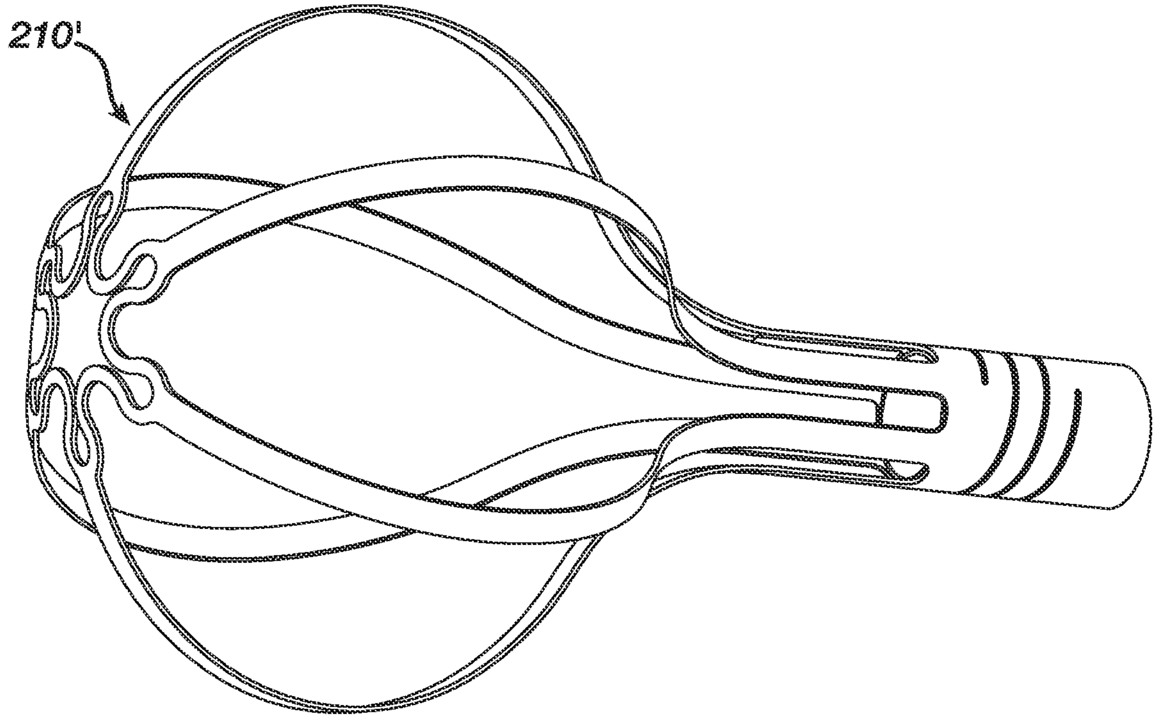
FIG. 5F illustrates a spine assembly after shape setting of the spines in FIG. 5E into a spheroidal basket like shape, in accordance with an embodiment of the present invention.

The spine assembly 210 can be physically connected to the tubular member 84 via a suitable technique such as adhesive or molding. In one embodiment shown here in FIG. 5C, eyelet 216*a* as well as locators 216*b* can be provided to aid in assembly as well as physical retention of the spines to the tubular member 84.

Where it is desired, a balloon BL can be provided as shown in FIG. 5D inside the spine assembly 210' to ensure full expansion of the spine assembly 210' from a cylindrical form factor into a spheroidal form as shown in FIG. 5C. In the embodiment of FIG. 5C, the spine assembly can be made from a tubular cylindrical stock material so that the proximal portion 210A and distal portion 210B are of one-piece material. The tubular stock is cut into a desired shape for the spine assembly 210' as shown in FIG. 5E. Thereafter, the cut tube can be shape set (or heat set) as is known by those skilled in the art to provide for the spheroidal spine configuration shown in FIG. 5F.

Figure 6A:
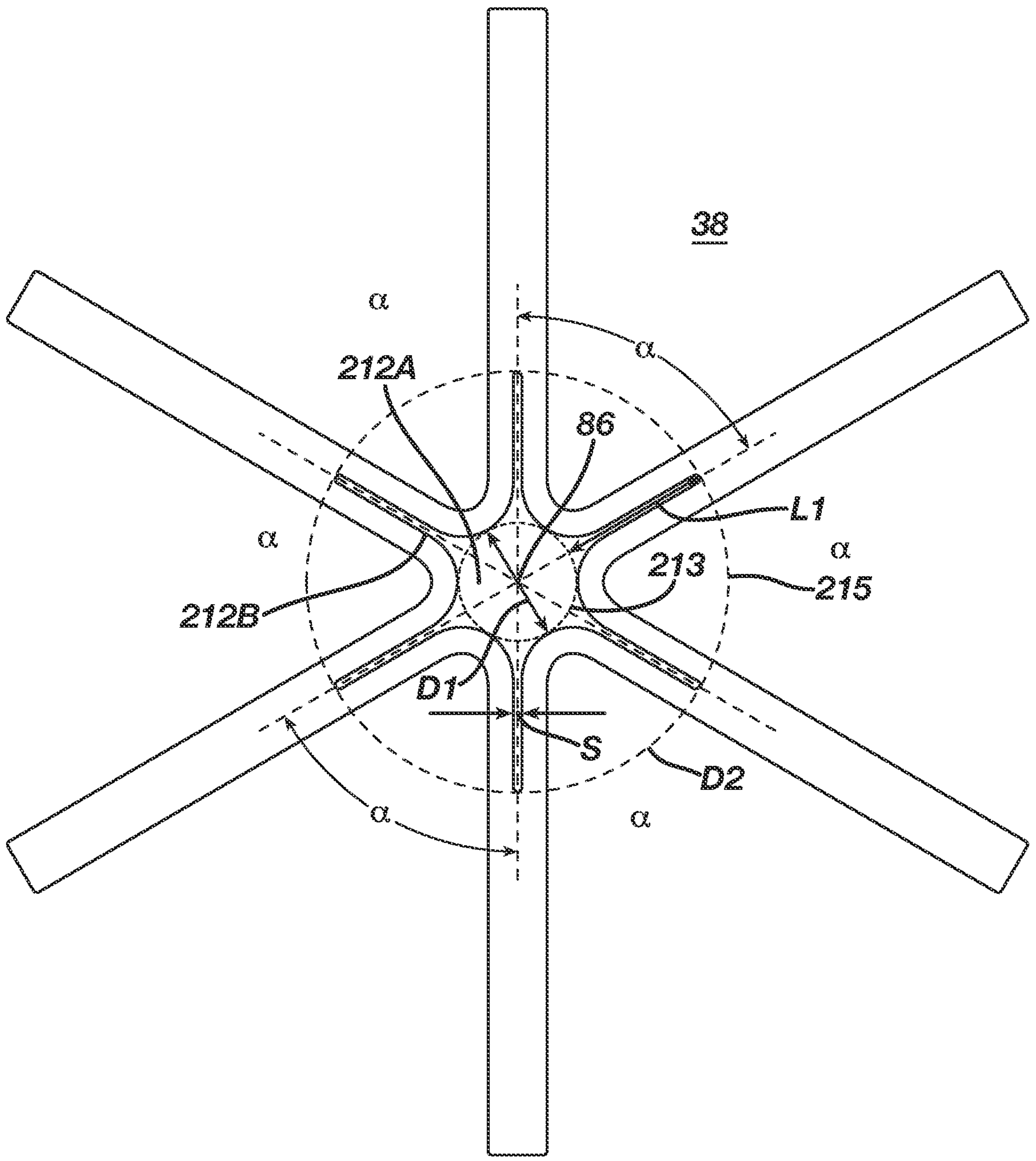
FIGS. 6A through 6E are schematic pictorial illustrations of central spine intersections, in accordance with an embodiment of the present invention.
Figure 6B:
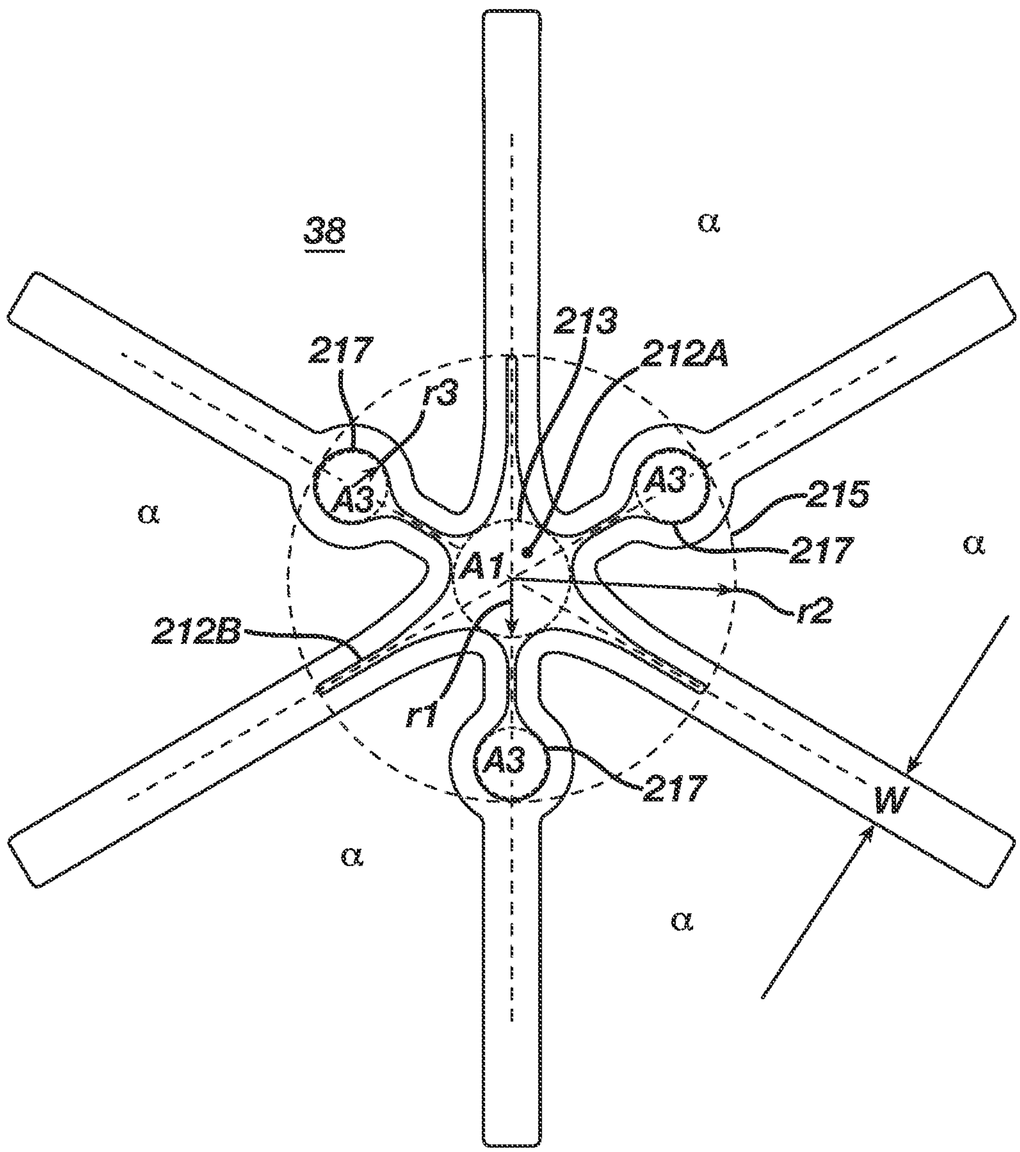

FIGS. 6A through 6E are schematic pictorial illustrations of top-down views of basket assembly 38, showing various examples of one or more cutouts 212 on central spine intersection 211. As shown, intersection 211 can include a single discrete cutout 212A, as shown in FIGS. 6A and 6B. Alternatively, intersection 211 can include two or more cutouts 212B, as provided as an example in FIGS. 6C and 6D. The one or more cutouts 212A, 212B can include a variety of patterns, such as centrosymmetric (i.e., symmetric with respect to a central point), and equiangular (i.e., including equal angles) to allow for equal bending among the spines 214 as well as disproportional and asymmetric to allow for unequal bending of spines 214 to alter structural stability. In certain instances, when basket assembly 38 includes an even number of spines 214, the pattern of the one or more cutouts 212 can alter between every other spine, as illustrated in FIG. 6B. In some examples, one or more cutouts 212 can extend along a portion of each spine 214. Each of the designs illustrated in FIGS. 6A-6E will be discussed separately.

In FIG. 6A, the distal end of the basket assembly 38 has an open cutout 212 which is a combination of a central opening 212A (substantially approximated by a virtual circle 213 with diameter D1) and the groove 212B for each spine (giving a total of six grooves 212B). Each spine is disposed generally equiangularly about the longitudinal axis of a predetermined angle $\alpha$ between any two spines. Each groove 212B has groove width S that extend approximately a length L1 from the circumference of virtual circle D1 so that a virtual circle 215 with diameter D2 is contiguous to the grooves 212B. The second virtual circle 215 has a diameter D2 approximately 3.6 times that of the diameter D1 of the first virtual circle 213. In one embodiment, the cut-out 212 (represented by center cut-out 212A and open grooves 212B) has a negative area of about 1.9 mm-squared with the diameter of the virtual circle 213 of about 1.1 mm and the virtual circle 215 of about 4 mm such that each open groove 212B has a width S of about 0.08 mm extending for about 1.5 mm from the virtual circle 213 so that the negative area defined by all the cut-outs in this design includes approximately 1.9 mm-squared.

In FIG. 6B, the basket 38 has its distal portion configured to have an open center 212A that radiates into each of the six spines 214. The open center 212A has a first area A1 that can be approximated by a virtual circle with radius r1. Three spines approximately 120 degrees apart have tapering grooves 212B extending back toward the proximal portion of basket 38. Three other spines approximately 120 degrees apart have large apertures 217 with area A3 disposed towards the proximal portion of the basket 38. The cut-out area A3 can be approximated by a virtual circle with radius r3 and disposed on the spines 214 such that the apertures 217 are contiguous to the inside circumference of virtual circle 215 with radius r2. In this configuration, each third area A3 is about ¼ of the open first area A1 while the total negative surface area of the entire cut-out includes approximately 1.6 times the first open area of empty space A1 and the second area A2 (calculated with radius r2) includes approximately 7 times the first area A1. Additionally, the second area A2 includes approximately 36 times third area A3. The radius r3 includes approximately 0.4 times that of radius r1 while radius r2 includes approximately 2.8 times that of radius r1. In one exemplary embodiment, first open area of empty space A1 includes approximately 2 mm-squared; second area A2 (as defined by radius r2) being approximately 15 mm-squared; third area A3 includes approximately 0.4 mm-squared; total area of all cut-outs includes approximately 3.5 mm-squared; radius r1~0.8 mm; r2~2.2 mm; and r3~0.4 mm.

Figure 6C:
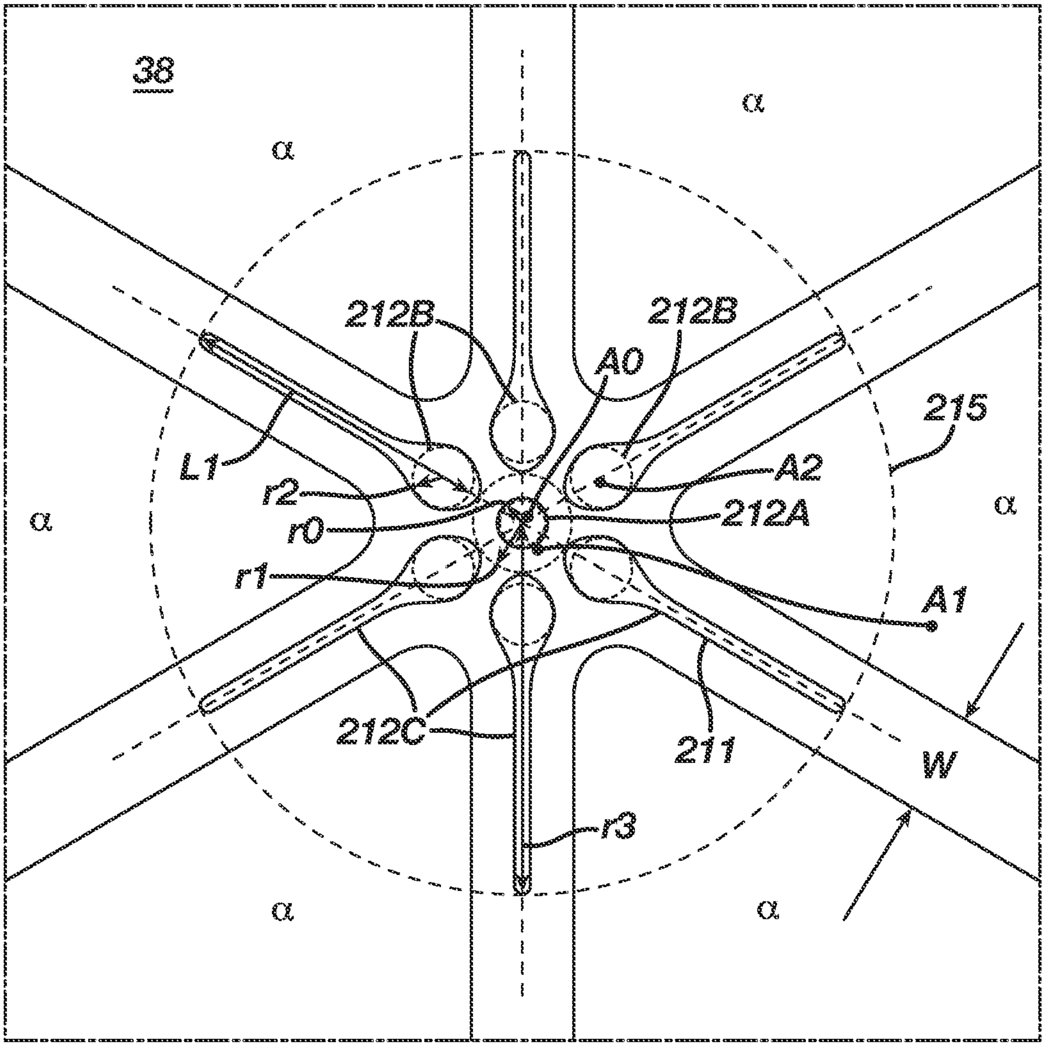

In FIG. 6C, this design has a small aperture 212A disposed at the center (coincident with longitudinal axis 86) of the basket 38 with a tadpole shaped cut-out 211 disposed on each of the spines 214. Each tadpole cut-out 211 is defined by an aperture cut-out 212B that is merged with grooved cut-out 212C. It is noted that while aperture 212A or 212B is shown approximating the of a circle, it is within the scope of this invention to have cut-out opening 212A or 212B in any shape as long as each aperture 212A or 212B has the requisite negative area. In the event the aperture 212A is configured as a circle, aperture 212A has central void A0 (of negative area) that can be approximated by a first virtual circle with radius r0 while each aperture 212B has a second area A2 that can be represented by a second virtual circle with radius r2. The apertures 212B (or the "heads" of the tadpole cut-outs) are radially arrayed so that apertures 212B are contiguous to a first virtual circle with radius r1. The second virtual circle may have a second radius r2 of 1.2 times that of the radius r0 of the first virtual circle representing aperture 212A while the first virtual circle r1 may have radius r1 of approximately 1.5 times that of the radius of the central virtual circle r0. The tail or grooved opening 212C of the "tails" extends towards the proximal end of the basket 38 for a length L1 so that each tail is contiguous to an inside circumference of a third virtual circle 215. Slot length L1 includes approximately 6-10 times that of the first radius r1. Third virtual circle 215 may have a radius r3 extending from the longitudinal axis 86 where radius r3 includes approximately 10-15 times that of either first radius r1 or central radius r0. In the exemplary embodiment (amongst many), the negative area of each of the tadpole cut-out 211 includes approximately 0.2 mm-squared while the negative area of center aperture 212A includes approximately 0.05 mm-squared so that the total negative area defined by all of the cut-outs includes approximately 1.4 mm-squared. In the same exemplary embodiment, the central radius r0 may be approximately 0.13 mm, the second radius r2 may be approximately 0.2 mm, and the first radius r1 may be approximately 0.23 mm.

Figure 6D:
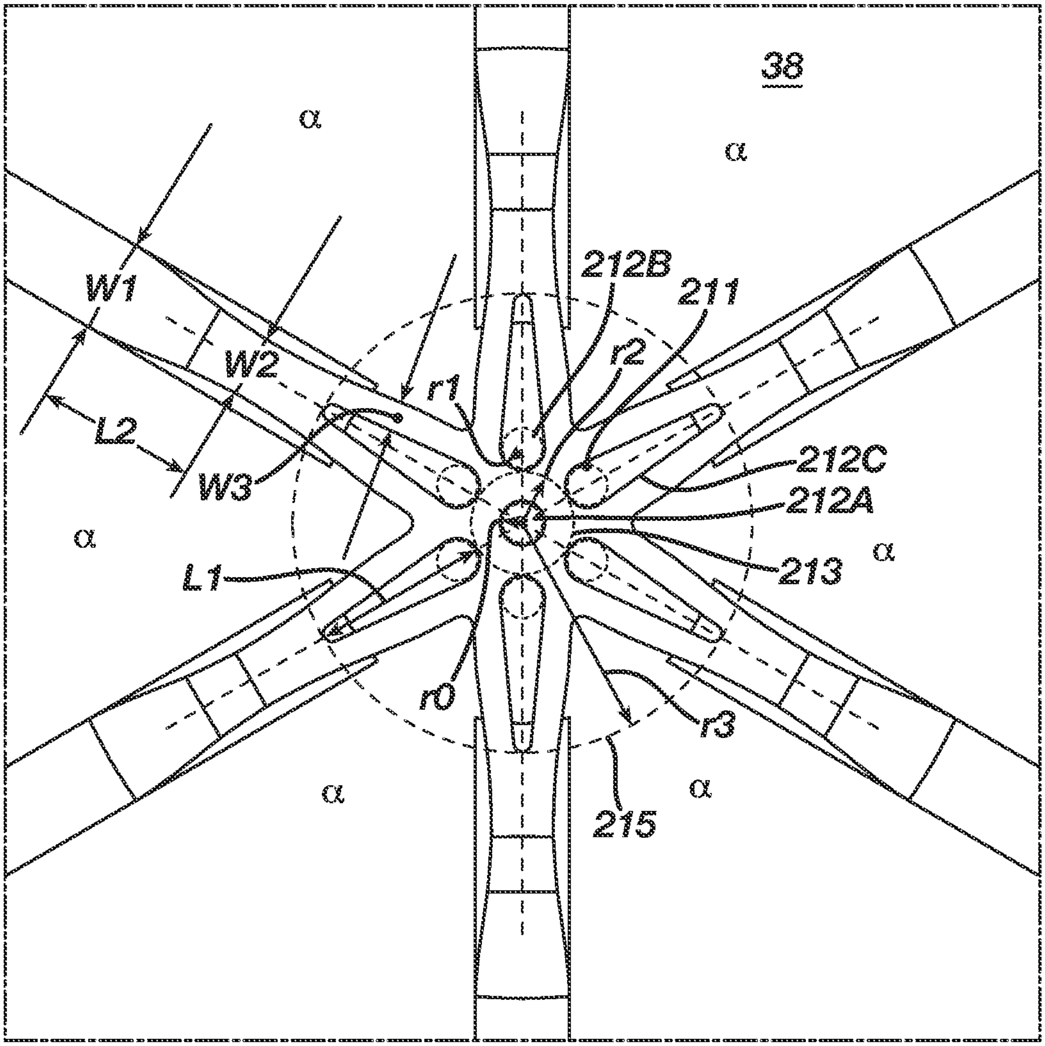

In FIG. 6D, the design of the basket 38 is provided with an aperture 212A at approximate center (i.e., axis 86) of the spines 214. Each spine 214 is provided a comet-shaped cut-out 211 with head portion 212B with an open tapered slot tail 212C tapering towards the proximal portion of each spine 214. The comet-shaped cut-outs 212B are arrayed so that the distal head portion 212B of the cut-out 211 are contiguous to an outside circumference of second virtual circle 213 while the proximal slotted opening 212C of the cut-outs 211 are contiguous on the inside circumference of third virtual circle 215. Where the aperture 212A is configured as a circular hole located on central axis 86 with radius r0 where the first radius r1 includes approximately 90% of the central radius r0, the second virtual circle 213 may have a second radius r2 of approximately 2.5 times that of central radius r0 while the third virtual circle 215 has a radius r3 of approximately 10 times that of the central radius r0 (all measured from center axis 86). Spine 214 has a first width W1 that tapers towards central axis 86 to a narrower second spine width W2 of approximately 66% of first spine width W1 at its narrowest point before being sub-divided by comet shaped cut-out 212B into two narrower spine arms with each arm including a third spine width W3 of approximately ⅓ that of the width W1. The comet shaped cut-out 212B has a length L1 along the spine of approximately 1.8 times that of the largest spine width W1.

Figure 6E:
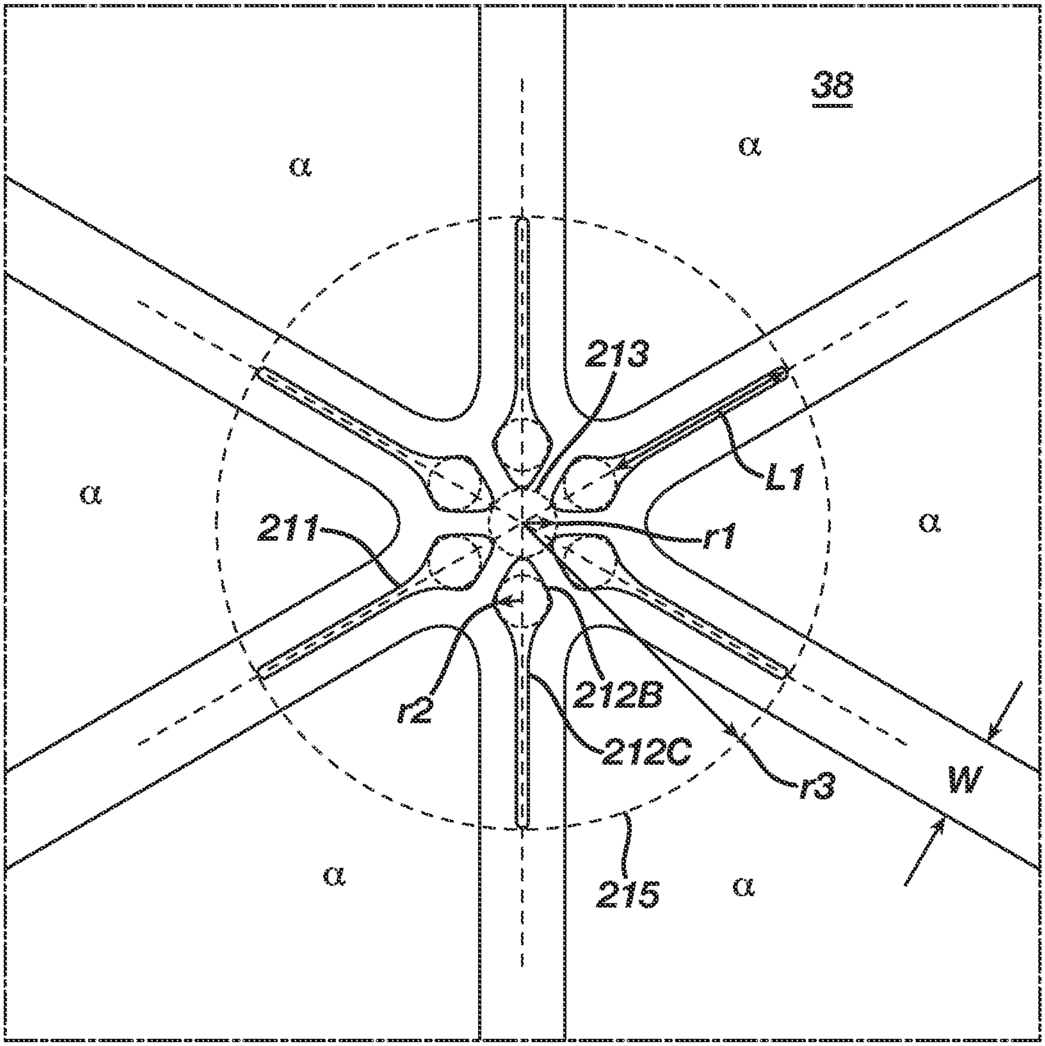

In FIG. 6E, the center (on axis 86) of the radiating spines 214 for basket 38 does not have a cut-out so that there is no void at the center of the basket to act as sharp edge surface (at the edge of such center aperture) against biological tissues. To allow for consistent folding of the spines near the distal portion of basket 38, each spine is provided with a tadpole shaped cut-out 211 that extends from the head portion 212B to tail portion 212C. The head portions 212B are arrayed so that the head portions 212B are contiguous to an outside circumference of first virtual circle 213 with radius r1. Each head portion 212B has a negative surface area that can be approximated by a second virtual circle with radius r2 of approximately 90% of the first radius r1. The tail portions 212C are bounded by a third virtual circle 215 with a radius r3 approximately 10 times that of the first radius. The length L1 of each of the tail portion includes approximately 1.5 times that of the width W1 of the spine 214. In one exemplary embodiment (out of many), the total negative area of the six cut-outs includes approximately 1.5 mm-squared.

The spines 214 can be folded or otherwise bent such that each respective attachment end 216 of the spine 214 can be inserted into the distal end 85 of the tubular shaft 84 (as shown in FIG. 2B) and relief lands 96 of spine retention hub 90 (not shown). Although not shown in FIGS. 5A and 5B, it will be appreciated that electrodes 40 can be attached to spines 214 before the spines are inserted into the tubular shaft 84 to form the basket assembly 38. As stated previously, the spines 214 can include a flexible, resilient material (e.g., a shape-memory alloy such as nickel-titanium, also known as Nitinol) that can enable the basket assembly 38 to transition to its expanded form (as shown in FIG. 2A) when the basket assembly 38 is deployed from tubular shaft 84. As will become apparent throughout this disclosure, spines 214 can be electrically isolated from electrode 40 to prevent arcing from electrode 40 to the respective spine 214.

As will be appreciated by one skilled in the art with the benefit of this disclosure, basket assembly 38 shown in FIGS. 2A through 2C including spines 214 formed from a single sheet of planar material and converging at a central intersection is offered merely for illustrative purposes and the disclosed technology can be applicable to other configurations of basket assemblies 38. For example, the described configuration of the basket spine assemblies can be obtained via laser cutting a nitinol tube and heat treating the spines from the tubular stock into substantially the planar form shown herein. As well, the disclosed technology can be applicable to basket assemblies 38 formed from a single spine 214 or multiple spines 214 with each spine 214 being attached at both ends. In other examples, the basket assembly 38 can include a central hub connecting the multiple spines 214 together at a distal end 39 of the basket assembly 38. In yet other examples, the basket assembly 38 can include a single spine 214 configured to form a spiral, multiple spines 214 configured to form a spiral, multiple spines 214 configured to form a tripod or multiple tripods, or any other shape of basket assembly 38. Thus, although FIGS. 2A through 2C illustrate a specific configuration of basket assembly 38, the disclosed technology should not be construed as so limited.

In the exemplary embodiments shown herein, the spines width W may have a nominal width of approximately 0.6 mm and can be as low as 0.2 mm or as large as 1.5 mm. The thickness of each spine can be nominally 0.09 mm and can vary from 0.05 mm to 0.2 mm. It should be noted that these values for width and thickness can vary depending on the stiffness desired.

Referring back to FIG. 2A through FIG. 2C, one or more electrodes 40 can be attached to spines 214 to form the basket assembly 38. In some examples, each electrode 40 can include electrically conductive material (e.g., gold, platinum and palladium (and their respective alloys)).

Turning to FIGS. 7A through 7J, electrode 40 can have a variety of cross-sectional shapes, curvatures, lengths, lumen number and lumen shape as provided as examples in electrodes 740A-740E. The electrodes 740A-740E are offered to illustrate various configurations of electrodes 40 that can be used with the medical device 22 but should not be construed as limiting. One skilled in the art will appreciate that various other configurations of electrodes 40 can be used with the disclosed technology without departing from the scope of this disclosure.

Each electrode 740A-740E can have an outer surface 774 facing outwardly from electrode 740 and an inner surface 776 facing inwardly toward electrode 740 where at least one lumen 770 is formed through electrode 740. The lumen 770 can be sized and configured to receive a spine 214 such that spine 214 can pass through electrode 740. Lumen 770 can be a symmetric opening through electrode 740A-740E and can be disposed offset with respect to a longitudinal axis L-L of the respective electrode. In other examples, lumen 770 can pass through electrode 740 in a generally transverse direction with respect to the longitudinal axis L-L of the respective electrode. Furthermore, lumen 770 can be positioned in electrode 740 nearer a bottom surface, nearer a top surface, or nearer a middle of electrode 740 depending on the particular configuration. In FIGS. 7A, 7C, and 7E through 7J, the top surface (upper side) is oriented toward the top of the drawing, the bottom surface (lower side) is oriented toward the bottom of the drawing, and the middle is between the top surface and the bottom surface. In other words, each electrode 740A-740E can include a lumen 770 that is offset with respect to a centroid of the electrode 740A-740E.

In addition, as shown in FIGS. 7A through 7F, electrodes 740A-740C can have a wire relief 772 forming a recess or depression in electrode 740 adjacent lumen 770 for one or more wires to pass through lumen 770 along with a respective spine 214. Relief 772 can be sized to provide room for a wire of electrode 740 to pass through electrode 740 such that electrode 740 can be in electrical communication with the control console 24.

Alternatively, or in addition thereto, wires can pass through a wire lumen 773 as shown in example electrodes 740D and 740E in FIGS. 7G through 7J. Although not depicted, electrodes 40 may include both a wire relief 772 adjacent lumen 770 and wire lumen 773. Such electrode may permit additional wires to pass through the electrode body.

Figure 7A:
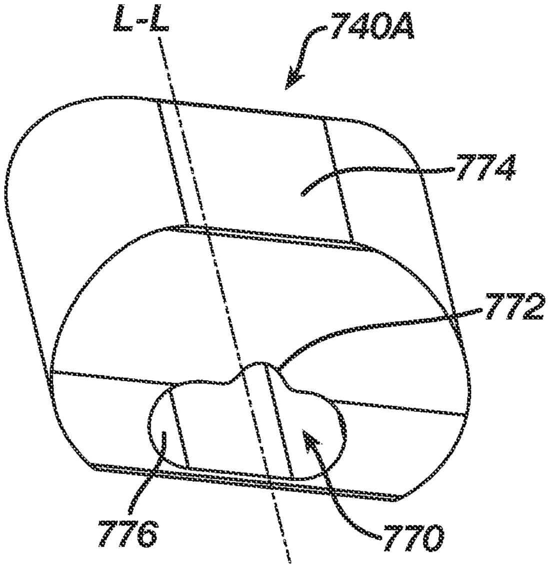
FIGS. 7A through 7J are schematic pictorial illustrations showing a perspective view of various example electrodes, in accordance with embodiments of the present invention.
Figure 7B:
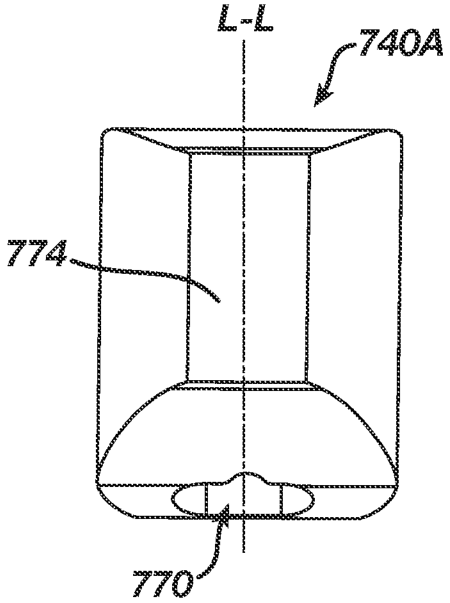
Figure 7C:
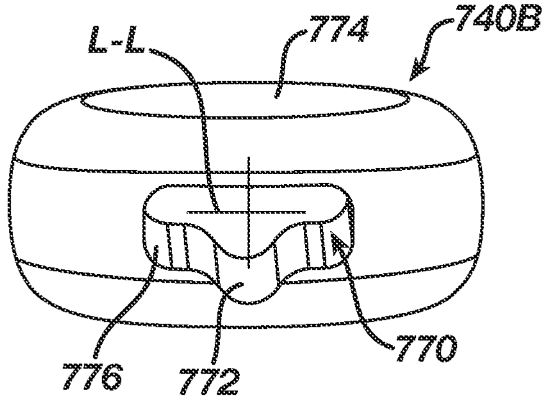
Figure 7D:
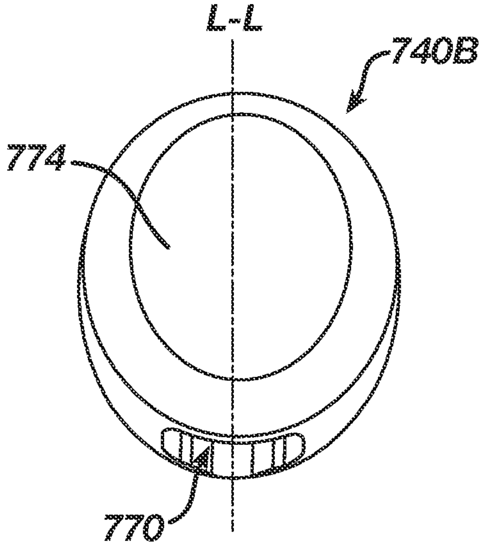
Figure 7E:
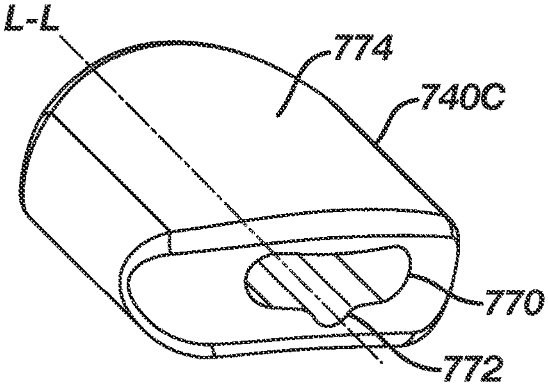
Figure 7F:
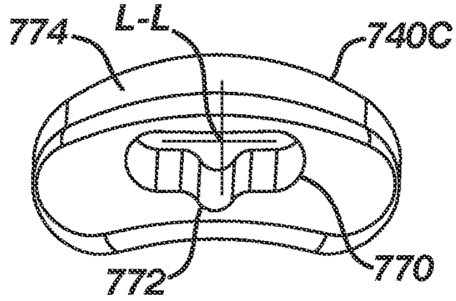
Figure 7G:
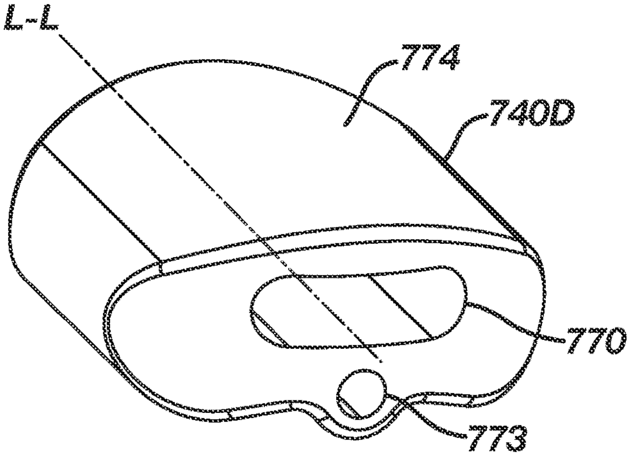
Figure 7H:
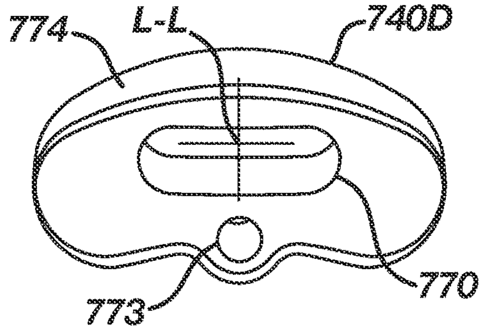
Figure 7I:
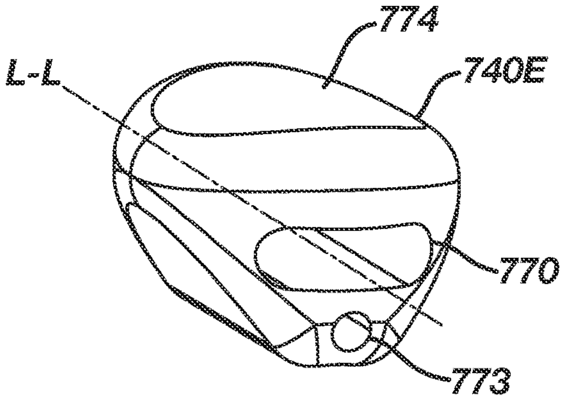
Figure 7J:
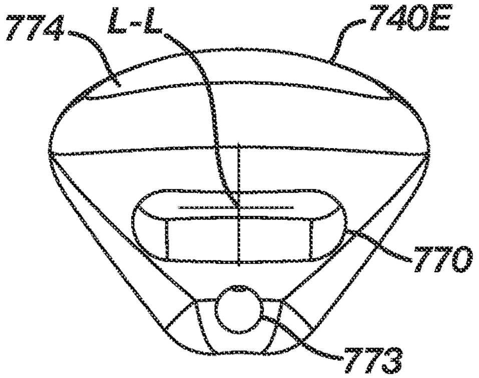

As shown in FIGS. 7A-7J, the electrodes 740A-740E can include various shapes depending on the application. For example, as illustrated in FIGS. 7A and 7B, the electrode 740A can have a substantially rectangular cuboid shape with rounded edges. In other examples, the electrode 740B can have a substantially ovoid shape (as illustrated in FIGS. 7C and 7D), the electrode 740C, 740D can have a contoured shape including a convex side and a concave side (as illustrated in FIGS. 7E through 7H), or the electrode 740E can have a contoured shape including substantially more material proximate an upper side than a lower side of the electrode 740E (as illustrated in FIGS. 71 and 7J). As will be appreciated by one of skill in the art, the various example electrodes 740A-740E shown in FIGS. 7A-7J, and described herein, are offered for illustrative purposes and should not be construed as limiting.

Figure 8A:
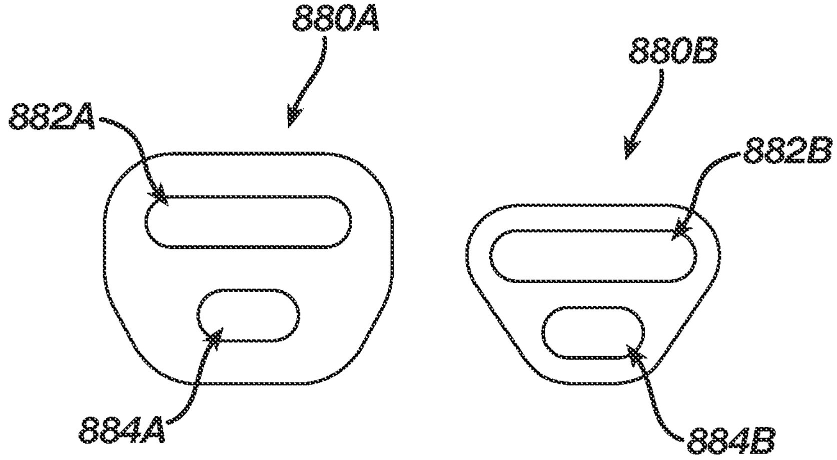
FIGS. 8A and 8B are schematic pictorial illustrations showing various insulative jackets of a given medical device, in accordance with embodiments of the present invention.
Figure 8B:
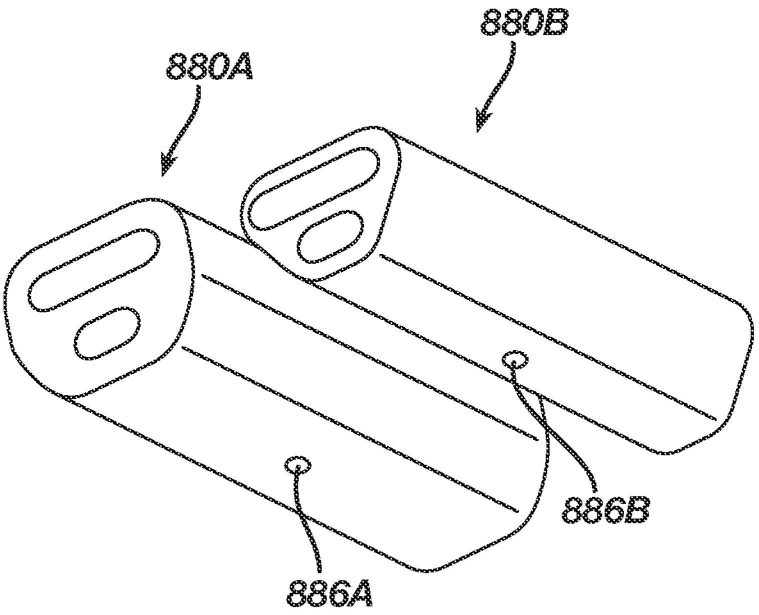

FIGS. 8A and 8B are schematic pictorial illustrations showing various insulative jackets 880A, 880B of a given medical device 22, in accordance with embodiments of the present invention. FIG. 8A is a front view while FIG. 8B is a perspective view of insulative jackets 880A, 880B. Insulative jackets 880A, 880B can be made from a biocompatible, electrically insulative material such as polyamide-polyether (Pebax) copolymers, polyethylene terephthalate (PET), urethanes, polyimide, parylene, silicone. In some examples, insulative material can include biocompatible polymers including, without limitation, polyetheretherketone (PEEK), polyglycolic acid (PGA), poly(lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response. Insulative jackets 880A, 880B may also include one or more additives or fillers, such as, for example, polytetrafluoroethylene (PTFE), boron nitride, silicon nitride, silicon carbide, aluminum oxide, aluminum nitride, zinc oxide, and the like. Insulative jacket 880A, 880B can help to insulate a spine 214 and/or wires passing through insulative jacket 880A, 880B from electrode 40 to prevent arcing from electrode 40 to the spine 214 and/or mechanical abrasion of wires passing through insulative jacket 880A, 880B.

As illustrated in FIGS. 8A and 8B, insulative jackets 880A, 880B, can include a cross-sectional shape that is substantially trapezoidal. The insulative jacket may consist of a single lumen or multi-lumen configuration. Multi-lumen jackets may be configured such that the alloy frame and wires share a single lumen while the second lumen may be used for irrigation. The alloy frame and wires may occupy separate lumens, also, as described. The current embodiment does not utilize irrigated jackets. For these designs, the insulative jackets may be continuous (individual sleeves extending from proximal to distal end of each alloy frame strut), segmented (bridging between electrode gaps), or a combination of both. Furthermore, insulative jacket 880A, 880B can include a first lumen 882A, 882B and a second lumen 884A, 884B. First lumen 882A, 882B can be configured to receive spine 214 while second lumen 884A, 884B can be configured to receive a wire, or vice-versa. In other examples, first lumen 882A, 882B and second lumen 884A, 884B can each be configured to receive one or more wires that can be connected to one or more electrodes 40. Furthermore, as illustrated in FIG. 8B, insulative jacket 880A, 880B can include an aperture 886A, 886B through which a wire can be electrically connected to electrode 40. Although illustrated in FIG. 8B as being proximate a bottom of insulative jacket 880A, 880B, aperture 886A, 886B can be positioned proximate a top or side of insulative jacket 880A, 880B. Furthermore, insulative jacket 880A, 880B can include multiple apertures 886A, 886B with each aperture being disposed on the same side of insulative jacket (i.e., top, bottom, left, right) or on different sides of the insulative jacket depending on the application.

Figure 9A:
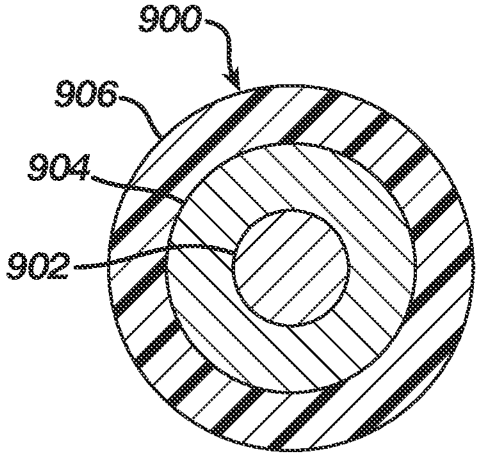
FIGS. 9A and 9B are schematic pictorial illustrations showing cross-sectional views of a given wire of a medical probe, in accordance with an embodiment of the present invention.
Figure 9B:
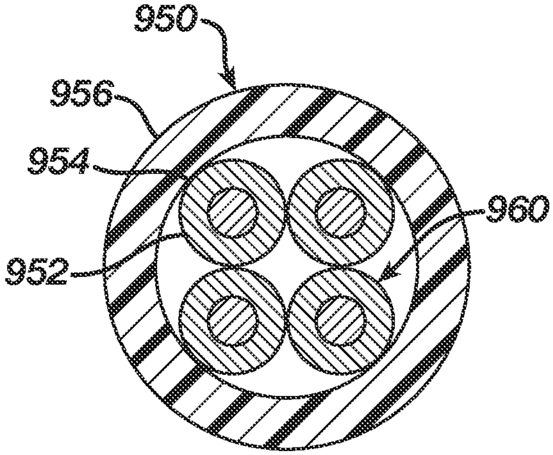

FIGS. 9A and 9B are schematic pictorial illustrations showing cross-sectional views of a given wire 900, 950 that can be connected to a given electrode 40, in accordance with an embodiment of the present invention. FIG. 9A illustrates a solid core wire 900. FIG. 9B illustrates a stranded wire 950. Each wire 900, 950 can extend through at least a portion of tubular shaft 84 and tubular shaft 84. Solid core wire 900 can include an electrically conductive core material 902 and an electrically conductive cover material 904 circumscribing electrically conductive core material 902. Likewise, stranded wire 950 can include strands each including an electrically conductive core material 952 and an electrically conductive cover material 954 circumscribing the electrically conductive core material 952. Each wire 900, 950 can include an insulative jacket 906 circumscribing the conductors. The wires 900, 950 can be configured to withstand a voltage difference of adjacent wires sufficient to deliver IRE pulses. Preferably, the wires 900, 950 can withstand at least 900V, and more preferably at least 1,800V between adjacent wires. To reduce likelihood of dielectric breakdown between conductors of adjacent wires, electrically conductive cover material 904, 954 can have a lower electrical conductivity compared to core material 902, 952.

Insulative jacket 906 can be configured to have a temperature rating between 150 and 200 degrees Centigrade so that the electrically insulative jacket 906 melts or degrades (e.g., chars and crumbles) during soldering of wire 900 to electrodes 40 (e.g., at a temperature of 300 degrees Centigrade) and therefore insulative jacket 906 of wire 900 does not need to be mechanically stripped. In other examples, insulative jacket 906 can have a temperature rating greater than 200 degrees Centigrade to prevent electrically insulating material 902 melting or degrading (e.g., charring and crumbling) during manufacture of medical probe 22 and/or during use. Insulative jacket 906 can be mechanically stripped from wire 900 prior to wires 900 being electrically connected to electrodes 40.

Figure 10:
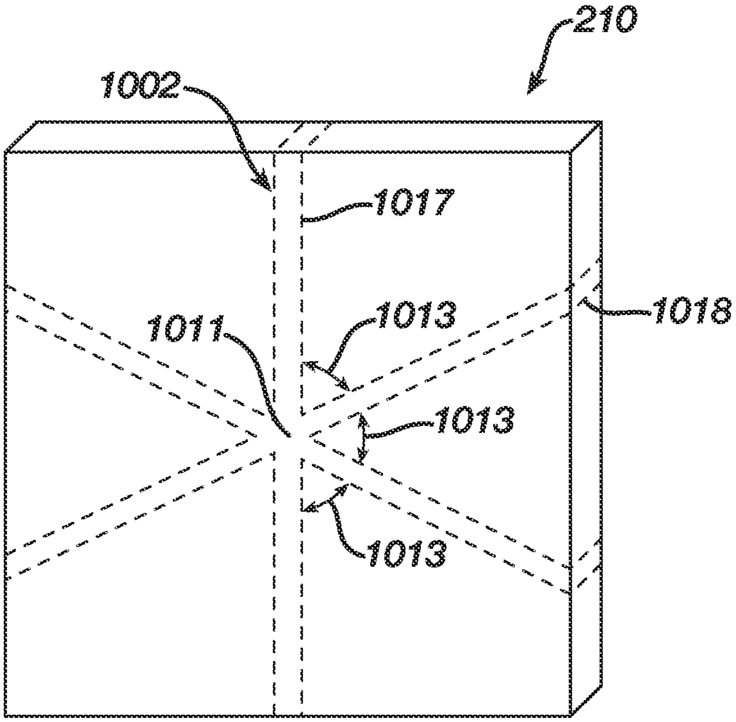
FIG. 10 is a schematic pictorial illustration of a method of cutting a plurality of linear spines from a planar sheet of material, in accordance with an embodiment of the present invention.
Figure 11A:
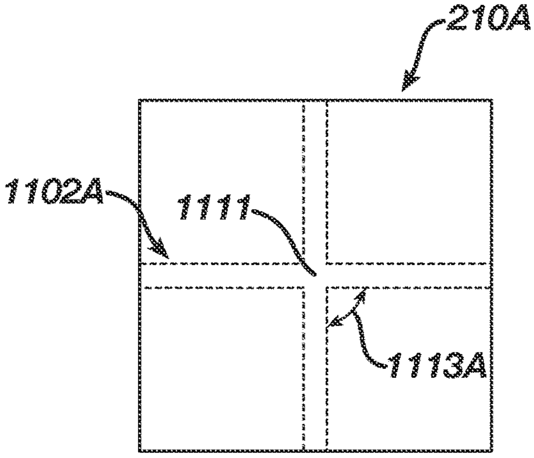
FIGS. 11A through 11D are schematic pictorial illustrations of a method of cutting a plurality of linear spines from a planar sheet of material, in accordance with an embodiment of the present invention.
Figure 11B:
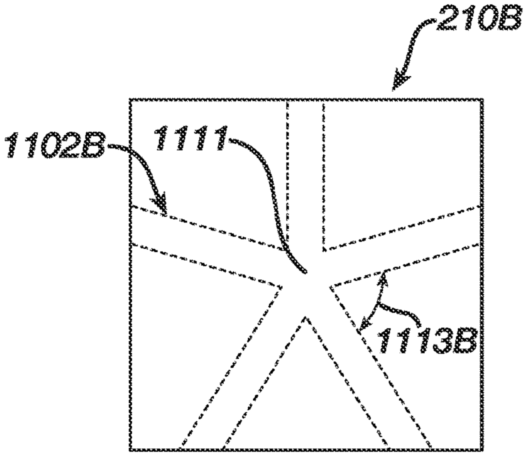
Figure 11C:
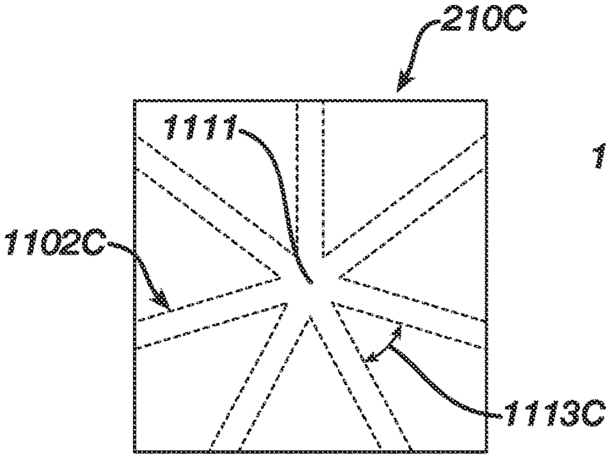
Figure 11D:
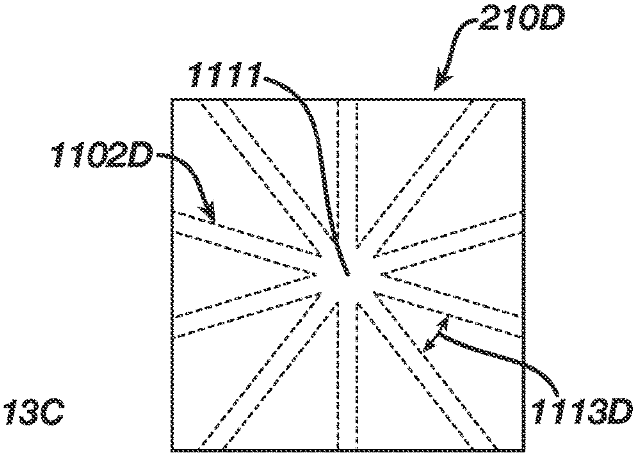

FIGS. 10-11D are schematic pictorial illustrations of cutting patterns for various linear spines patterns 1002 from a planar sheet of material 210. As described supra, planar sheet of material 210 can include a number of spines 214 ranging from about four to about ten spines. As illustrated in FIG. 10, planar sheet of material 210 can include central intersection 1011 and spine pattern 1002, which includes one or both of longitudinal scores 1017 and transverse scores 1018. In any of the embodiments disclosed herein, planar sheet of material 210 can also include a central intersection 1011 and spine patterns 1002 including an equiangular pattern 1013. Planar sheet of material 210 can include spine patterns including a number of spine patterns 1002 forming spines 214 in basket assembly 38. As would be understood by one of skill in the art, adjusting the number of spine patterns 1002 may impact a number of factors including, without limitation, stability, flexibility, surface contact, and ablation capacity of medical probe 22. FIGS. 11A through 11D provide example spine patterns 1102A, 1102B, 1102C, 1102D, although additional spine patterns are contemplated. Similar to the above planar sheet of material 210, spine patterns 1102A-1102D can include a respective central intersection 1111 and a respective equiangular pattern 1113A-1113D. As would be appreciated by one of skill in the art, as the number of spines added to spine pattern 1102A-1102D, the angle for equiangular pattern 1113A-1113D may change. In each of these examples provided, planar sheet of material 210A, 210B, 210C, 210D may also include central intersections and spine patterns including equiangular patterns. Although not depicted in FIG. 11A-11D, planar sheet of material 210A-210D can include one or both of longitudinal scores 1117 and transverse scores 1118.

Figure 12A:
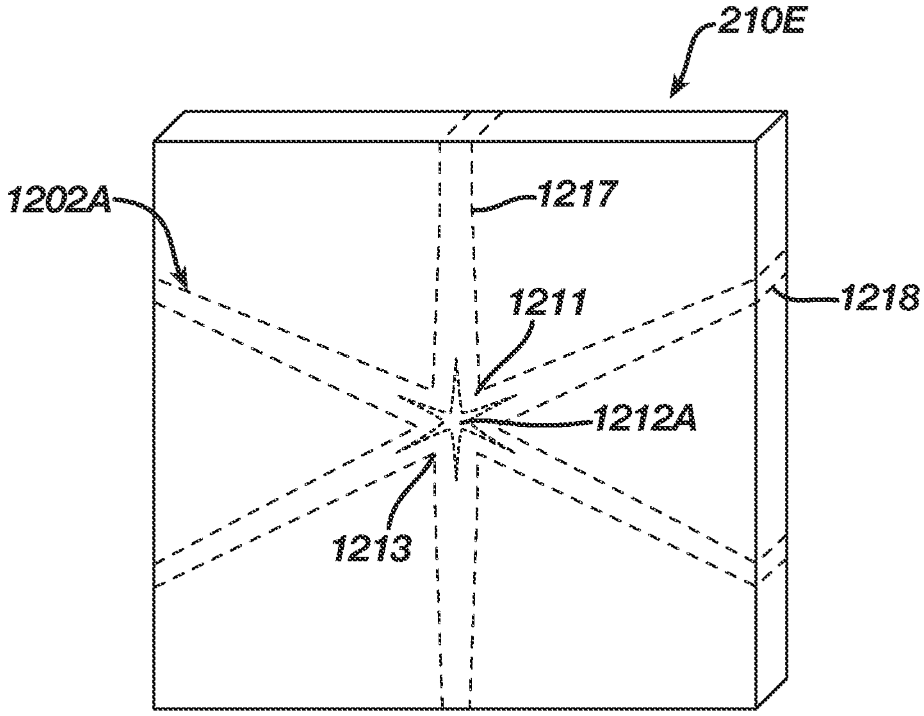
FIGS. 12A and 12B are schematic pictorial illustrations of a method of cutting a plurality of linear spines including one or more cutouts at a central spine intersection from a planar sheet of material, in accordance with an embodiment of the present invention.
Figure 12B:
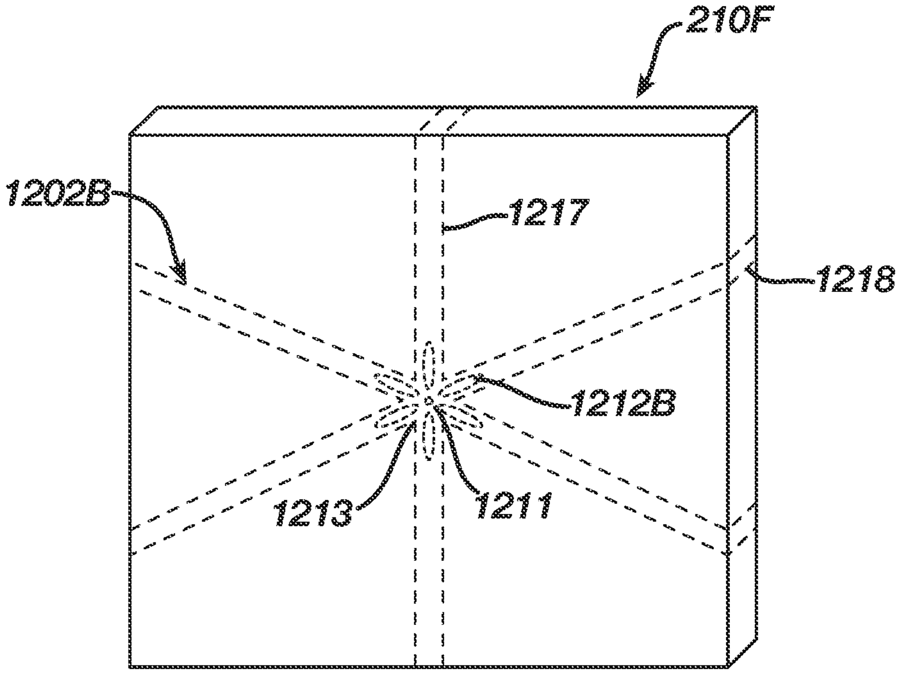

FIGS. 12A and 12B are schematic pictorial illustrations of cutting patterns for various linear spine patterns including one or more cutouts at a central spine intersection from a planar sheet of material. As described supra, planar sheet of material 210E, 210F may include a spine pattern 1202A including one cutout 1212A at central intersection 1211 or a spine pattern 1202B including two or more cutouts 1212B at central intersection 1211. As illustrated in FIGS. 12A and 12B, planar sheet of material 210E and 210F can include one or both of longitudinal scores 1217 and transverse scores 1218.

Figure 13:
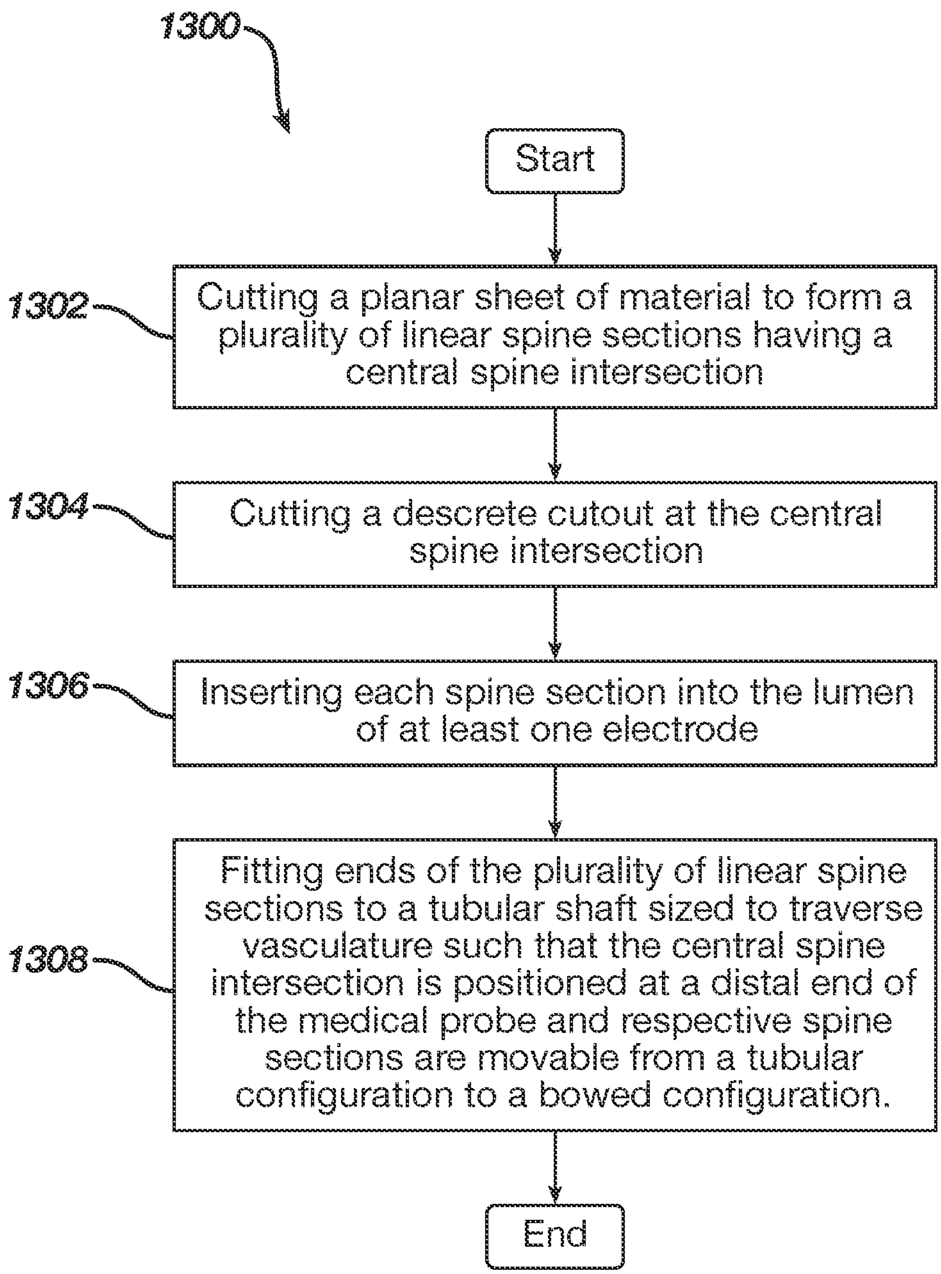
FIG. 13 is a flowchart illustrating another method of assembling a basket assembly, in accordance with an embodiment of the present invention.

FIG. 13 is a flowchart illustrating a method 1300 of manufacturing a basket assembly 38, in accordance with an embodiment of the present invention. Method 1300 can include cutting 1302 a planar sheet of material 210 to form a plurality of linear spines 214 including a central spine intersection 211. Cutting 1302 the plurality of linear spines 214 can include cutting from a pattern 1002 (or 1102A-1102D) including longitudinal and transverse scores 1017, 1018. The planar sheet of resilient material can include shape-memory alloy such as nickel-titanium (also known as Nitinol), cobalt chromium, or any other suitable material. Method 1300 can include cutting 1304 a discrete cutout 214 at the central spine intersection 211. As described supra, the discrete cutout 214 can be a single cutout or two or more cutouts. In addition, the one or more discrete cutouts can be cut in a pattern to extend along at least a portion of each spine. In some examples, steps 1302 and 1304 may occur as simultaneous steps or as a sequence of steps. As an alternative to steps 1302 and 1304, metallic strands can be shaped similar to the pattern formed by cutting the planar sheet in steps 1302 and 1304.

Method 1300 can include inserting 1306 each spine into a lumen of at least one electrode. The electrodes can be positioned such that the electrodes are offset between electrodes on adjacent spines. Method 1300 can include fitting 1308 ends of the plurality of linear spines to a tubular shaft sized to traverse vasculature such that the central spine intersection is positioned at a distal end of the medical probe and respective spines are movable from a tubular configuration to a bowed configuration. As will be appreciated by one of skill in the art including the benefit of this disclosure, fitting 1308 an end of the spine into a tubular shaft can include attaching the spine 214 to a spine retention hub 90. Furthermore, the spine retention hub 90 and/or the spine 214 and the tubular shaft 84 can be inserted into a flexible insertion tube 30 to form the medical probe 22

In some examples, the method can also include forming an approximately spheroid or oblate-spheroid shape with the linear spines. Method 1300 can further include electrically connecting the wire to the one or more electrodes. Method 1300 can also include disposing an insulative sleeve over the linear spines and within the lumen of the respective electrode.

As will be appreciated by one skilled in the art, method 1300 can include any of the various features of the disclosed technology described herein and can be varied depending on the particular configuration. Thus, method 1300 should not be construed as limited to the particular steps and order of steps explicitly described herein. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

The disclosed technology described herein can be further understood according to the following clauses:

Clause 1: A medical probe, comprising: a tubular shaft including a proximal end and a distal end, the tubular shaft extending along a longitudinal axis; an expandable basket assembly proximate the distal end of the tubular shaft, the basket assembly comprising a single unitary structure that includes a plurality of linear spines formed from a planar sheet of material, the spines converging at a central spine intersection, the central spine intersection including one or more cutouts that allows for bending of the spines, each spine including a respective end connected to the distal end of the tubular shaft, the central spine intersection being positioned on the longitudinal axis at a distal end of the basket assembly; and one or more electrodes coupled to each of the spines, each electrode defining a lumen through the electrode so that a spine extends through the lumen of each of the one or more electrodes.

Clause 2: The medical probe according to Clause 1, wherein the plurality of linear spines extend from the central spine intersection in an equiangular pattern such that respective angles between respectively adjacent spines are approximately equal.

Clause 3: The medical probe according to Clause 1 or 2, wherein the expandable basket assembly comprises four to ten spines of the plurality of spines.

Clause 4: The medical probe according to Clause 3, wherein the expandable basket assembly comprises exactly six spines of the plurality of spines.

Clause 5: The medical probe according to Clause 1, wherein the expandable basket assembly includes approximately spherical.

Clause 6: The medical probe according to Clause 1, wherein the expandable basket assembly includes approximately oblate-spheroid.

Clause 7: The medical probe according to any one of Clauses 1-6, further comprising a spine retention hub disposed proximate the distal end of the tubular shaft, the spine retention hub comprising a cylindrical member including a plurality of relief lands disposed on the outer surface of the cylindrical member to allow each spine to be fitted into a relief land and retained therein, the retention hub further includes at least one electrode disposed at a distal portion of the retention hub.

Clause 8: The medical probe according to Clause 7, wherein the electrode lumen is disposed offset with respect to a longitudinal axis of the electrode.

Clause 9: The medical probe according to any one of Clauses 1-8, wherein the expandable basket assembly comprises at least one discrete cutout located proximate the central spine intersection.

Clause 10: The medical probe according to any one of Clauses 1-8, wherein the one or more cutouts comprise a centrosymmetric pattern.

Clause 11: The medical probe according to any one of Clauses 1-8, wherein the one or more cutouts comprise an equiangular pattern.

Clause 12: The medical probe according to any one of Clauses 1-8, wherein the one or more cutouts extend along at least a portion of each spine.

Clause 13: The medical probe according to any one of Clauses 1-12, wherein each electrode comprises a wire relief adjacent the lumen to allow for one or more wires to extend adjacent to the lumen.

Clause 14: The medical probe according to Clause 13, wherein the electrode lumen is disposed symmetrically about a longitudinal axis of the electrode.

Clause 15: The medical probe according to any one of Clauses 1-14, wherein the one or more electrodes are configured to deliver electrical pulses for irreversible electroporation, the pulses including a peak voltage of at least 900 volts (V).

Clause 16: The medical probe according to any one of Clauses 13-15, further comprising irrigation openings disposed proximate the distal end of the tubular shaft, the irrigation openings configured to deliver an irrigation fluid to the one or more electrodes.

Clause 17: The medical probe according to any one of Clauses 1-16, further comprising a plurality of insulative sleeves each disposed over the respective given spine and within the lumen of the respective electrode.

Clause 18: The medical probe according to any one of Clauses 1-16 further comprising a plurality of insulative sleeves, each insulative sleeve comprising a first lumen through which the respective given spine extends and a second lumen through which an electrical wire extends, that the first and second lumens being distinct from each other, and each insulative sleeve extends within the lumen of the respective electrode.

Clause 19: The medical probe according to any one of Clauses 1-18, further comprising: a plurality of wires each electrically joined to a respective electrode of the one or more electrodes, wherein at least a portion of the wires of the plurality of the wires respectively comprises an electrically conductive core material comprising a first electrical conductivity, an electrically conductive cover material comprising a second electrical conductivity less than the first electrical conductivity, the electrically conductive cover material circumscribing the electrically conductive core material, and an insulative jacket circumscribing the electrically conductive cover material.

Clause 20: The medical probe according to any one of Clauses 1-19, further comprising: a plurality of wires each electrically joined to a respective electrode of the one or more electrodes, wherein at least a portion of the wires of the plurality of the wires respectively comprises a plurality of strands and an insulative jacket circumscribing the plurality of the strands, and wherein each strand of the plurality of strands respectively comprises an electrically conductive core material comprising a first electrical conductivity and an electrically conductive cover material comprising a second electrical conductivity less than the first electrical conductivity, the electrically conductive cover material circumscribing the electrically conductive core material.

Clause 21: The medical probe according to any one of Clauses 1-20, wherein the planar sheet of material comprises nitinol.

Clause 22: The medical probe according to any one of Clauses 1-20, wherein the planar sheet of material comprises cobalt chromium.

Clause 23: A method of constructing a medical probe, the method comprising: cutting a planar sheet of material to form a plurality of linear spines including a central spine intersection; cutting a discrete cutout at the central spine intersection; inserting each spine into a lumen of at least one electrode; and fitting ends of the plurality of linear spines to a tubular shaft sized to traverse vasculature such that the central spine intersection is positioned at a distal end of the medical probe and respective spines are movable from a tubular configuration to a bowed configuration.

Clause 24: The method according to Clause 23, further comprising cutting the plurality of linear spines from a pattern comprising longitudinal and transverse scores.

Clause 25: The method according to Clause 23 or 24, further comprising cutting at least two cutouts at the central spine intersection.

Clause 26: The method according to any one of Clauses 23-25, further comprising cutting a single discrete cutout at the central spine intersection.

Clause 27: The method according to Clause 26, further comprising cutting the single discrete cutout along at least a portion of each spine.

Clause 28: The method according to any one of Clauses 23-25, further comprising cutting each discrete cutout along at least a portion of each spine.

Clause 29: The method according to any one of Clauses 23-28, further comprising offsetting the electrodes between adjacent spines.

Clause 30: The method according to any one of Clauses 23-29, wherein the linear spines form an approximately oblate-spheroid shape in the predetermined shape.

Clause 31: The method according to any one of Clauses 23-30, wherein each electrode comprises a relief adjacent the lumen to allow a wire to extend adjacent to the lumen.

Clause 32: The method according to Clause 31, wherein the wire is electrically insulated from the single spine.

Clause 33: The method according to any one of Clauses 31-32, further comprising electrically connecting the wire to the one or more electrodes.

Clause 34: The method according to any one of Clauses 32-33, wherein at least a portion of the wire comprises an electrically conductive core material comprising a first electrical conductivity, an electrically conductive cover material comprising a second electrical conductivity less than the first electrical conductivity, the electrically conductive cover material circumscribing the electrically conductive core material, and an insulative jacket circumscribing the electrically conductive cover material.

Clause 35: The method according to any one of Clauses 32-33, wherein at least a portion of the wire comprises a plurality of strands and an insulative jacket circumscribing the plurality of strands, and wherein each strand of the plurality of strands respectively comprises an electrically conductive core material comprising a first electrical conductivity and an electrically conductive cover material comprising a second electrical conductivity less than the first electrical conductivity, the electrically conductive cover material circumscribing the electrically conductive core material.

Clause 36: The method according to any one of Clauses 23-35, further comprising a separate lumen configured to receive a wire with insulation with the wire capable of delivering at least 900V without dielectric breakdown of the insulation.

Clause 37: The method according to any one of Clauses 23-36, wherein the one or more electrodes are configured to deliver electrical pulses for irreversible electroporation, the pulses including a voltage of at least 900 volts (V).

Clause 38: The method according to any one of Clauses 23-37, further comprising irrigation openings disposed proximate the distal end of the tubular shaft, the irrigation openings configured to deliver an irrigation fluid to an area proximate the one or more electrodes.

Clause 39: The method according to any one of Clauses 23-38, further comprising disposing an insulative sleeve over the linear spines and within the lumen of the respective electrode.

Clause 40: The method according to Clause 39, wherein the insulative sleeve comprises a first lumen through which a strut extends and a second lumen through which an electrical wire extends, the first and second lumens being distinct from each other.

Clause 41: The method according to any of Clauses 39 or 40, wherein a cross-sectional shape of each electrically insulative sleeve comprises a substantially trapezoidal shape.

Clause 42: The method according to any one of Clauses 23-41, wherein the electrode comprises an oblong body type electrode with the lumen extending through the oblong body.

Clause 43: The method according to any one of Clauses 23-41, wherein the electrode comprises a bulging-type electrode.

Clause 44: A spine basket member comprising: a plurality of spines extending radially from a central axis; and a cut-out defining a first open area of empty space proximate the central axis, the first open area of empty space approximating a first virtual circle including a first diameter from the central axis, the cut-out extending into each of the plurality of spines for a first length to define an open slot in each of the plurality of spines, each slot being contiguous to a circumference of a second virtual circle greater than the first virtual circle.

Clause 45: The spine basket member of Clause 44, wherein one of every other slots on the plurality of spines includes an aperture defining a third area smaller than the first open area of empty space.

Clause 46: The spine basket member of Clause 45, in which the second virtual circle defines a second area of approximately 36 times that of the third area.

Clause 47: The spine basket member of Clause 46, in which the second area comprises approximately 7 times the first open area of empty space.

Clause 48: The spine basket member of Clause 45, in which the third area is about ¼ of the open first area while the total negative surface area of the entire cut-out includes approximately 1.6 times the first open area of empty space.

Clause 49: The spine basket member of Clause 45, in which the third area comprises a circle with a radius includes approximately 0.4 times that of a first radius of the first virtual circle and a radius of the second virtual circle includes approximately 2.8 times that of the first radius.

Clause 50: The spine basket member of Clause 49, in which the first open area of empty space comprises approximately 2 mm-squared, the second area being approximately 15 mm-squared and the third area includes approximately 0.4 mm-squared and a total area of all cut-outs includes approximately 3.5 mm-squared.

Clause 51: A spine basket member comprising: a plurality of spines extending radially from a solid central axis; and a tadpole shaped cut-out on each of the plurality of spines, each cut-out including a head portion contiguous to a circumference of a first virtual circle with a first radius disposed about the central axis, the head portion defining a negative area approximating a second virtual circle with a second radius, the head portion connected to a slotted tail portion extending for a first length along the spine and contiguous to an inside circumference of a third virtual circle including a third radius.

Clause 52: The spine basket member of Clause 51, in which the second radius includes approximately equal to that of a radius of the first virtual circle and the third radius includes approximately 8-15 times that of the radius of the first virtual circle.

Clause 53: The spine basket member of Clause 52, in which the first length of the slotted tail portion includes approximately 6-10 times that of the length of the radius of the first virtual circle.

Clause 54: The spine basket member of Clause 51, further comprising a cut-out disposed on the central axis to define a central negative area approximating a central circle including a central radius smaller than the first radius.

Clause 55: The spine basket member of Clause 51, in which the negative area of each of the tadpole cut-out includes approximately 0.2 mm-squared while the negative area of center aperture includes approximately 0.05 mm-squared so that the total negative area defined by all of the cut-outs includes approximately 1.4 mm-squared.

Clause 56: The spine basket member of Clause 51, in which central void radius comprises approximately 0.13 mm, the second radius comprises approximately 0.2 mm, and the first radius comprises approximately 0.23 mm.

Clause 57: The spine basket member of Clause 51, in which the cut-out defines a comet-shaped cutout with head portion with a slotted tapered tail extending to the proximal portion of each spine.

Clause 58: The basket shaped catheter of Clause 57, further comprising a circular hole located on the central axis of the spines with a central radius from the central axis.

Clause 59: The basket shaped catheter of Clause 58, wherein first radius includes approximately 90% of the central radius, the second virtual circle includes a second radius of approximately 2.5 times that of central radius while the third virtual circle includes a radius of approximately 10 times that of the central radius.

Clause 60: The spine assembly of Clause 59, wherein each spine includes a first spine width that tapers towards the central axis to a smaller second spine width and further sub-dividing by the comet shaped cut-out portion into two narrower spine arms running along the comet shaped cutout, each narrow spine arm including a third spine width.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A medical probe, comprising:

a tubular shaft including a proximal end and a distal end, the tubular shaft extending along a longitudinal axis;

an expandable basket assembly proximate the distal end of the tubular shaft, the expandable basket assembly comprising a single unitary structure that includes a plurality of linear spines formed from a planar sheet of material, the plurality of linear spines comprising a first plurality of linear spines and a second plurality of linear spines that alternate about the longitudinal axis, the plurality of linear spines converging at a central spine intersection, the central spine intersection including a cutout that allows for bending of the plurality of linear spines, each of the plurality of linear spines including a respective end connected to the distal end of the tubular shaft, the central spine intersection being positioned on the longitudinal axis at a distal end of the basket assembly, the cutout defining a first open area of empty space proximate the longitudinal axis, the first open area of empty space approximating a first virtual circle including a first diameter from the longitudinal axis, the cutout extending into each of the plurality of linear spines for a first length to define a first open slot defined in each of the first plurality of linear spines and a second open slot defined in each of the second plurality of linear spines, each first open slot and each second open slot being contiguous to a circumference of a second virtual circle greater than the first virtual circle, each first open slot tapering in width from the first open area of empty space towards a proximal portion of the expandable basket assembly, each second open slot comprising a respective aperture that defines a third area of empty space such that each linear spine of the second plurality of linear spines bulges outwardly, in a width direction of each spine of the second plurality of spines, in a region proximate the respective aperture; and one or more electrodes coupled to each of the plurality of linear spines, each electrode defining a lumen through the electrode so that a spine of the plurality of linear spines extends through the lumen of each of the one or more electrodes.

2. The medical probe according to claim 1, wherein the plurality of linear spines extend from the central spine intersection in an equiangular pattern such that respective angles between respectively adjacent spines are approximately equal.

3. The medical probe according to claim 2, further comprising a spine retention hub disposed proximate the distal end of the tubular shaft, the spine retention hub comprising:

a cylindrical member including a plurality of relief lands disposed on an outer surface of the cylindrical member to allow each spine of the plurality of linear spines to be fitted into a relief land and retained therein; and at least one electrode disposed at a distal portion of the retention hub.

4. The medical probe according to claim 1, wherein the expandable basket assembly comprises at least one discrete cutout located proximate the central spine intersection.

5. The medical probe according to claim 4, wherein the one or more discrete cutouts extend along at least a portion of each spine.

6. The medical probe according to claim 1, wherein the one or more electrodes are configured to deliver electrical pulses for irreversible electroporation, the electrical pulses including a peak voltage of at least 900 volts (V).

7. A spine basket assembly comprising:

a plurality of spines extending radially from a central axis, the plurality of spines comprising a first plurality of spines and a second plurality of spines that alternate about the central axis;

a cut-out defining a first open area of empty space proximate the central axis, the first open area of empty space approximating a first virtual circle including a first diameter from the central axis, the cut-out extending into each of the plurality of spines for a first length to define a first open slot defined in each of the first plurality of spines and a second open slot defined in each of the second plurality of spines, each first open slot and each second open slot being contiguous to a circumference of a second virtual circle greater than the first virtual circle, each first open slot tapering in width from the first open area of empty space towards a proximal portion of the spine basket assembly, each second open slot comprising a respective aperture that defines a third area of empty space such that each spine of the second plurality of spines bulges outwardly, in a width direction of each spine of the second plurality of spines, in a region proximate the respective aperture; and one or more electrodes coupled to each of the spines of the plurality of spines.

8. The spine basket assembly of claim 7, wherein the third area of empty space of each aperture being smaller than the first open area of empty space.

9. The spine basket assembly of claim 8, in which the second virtual circle defines a second area of approximately 36 times that of the third area of empty space of each aperture.

10. The spine basket assembly of claim 9, in which the second area comprises approximately 7 times the first open area of empty space.

11. The spine basket assembly of claim 8, in which the third area of empty space of each aperture is about ¼ of the first open area of empty space while a total negative surface area of an entirety of the cut-out includes approximately 1.6 times the first open area of empty space.

12. The spine basket assembly of claim 8, in which the third area of empty space of each aperture comprises a circle with a radius includes approximately 0.4 times that of a first radius of the first virtual circle and a radius of the second virtual circle includes approximately 2.8 times that of the first radius of the first virtual circle.

13. The spine basket assembly of claim 12, in which the first open area of empty space comprises approximately 2 mm-squared, a second area defined by the second virtual circle being approximately 15 mm-squared and the third area includes approximately 0.4 mm-squared and a total area of all cut-outs includes approximately 3.5 mm-squared.

14. A method of constructing a medical probe, the method comprising:

cutting a planar sheet of material to form a plurality of linear spines including a central spine intersection, the plurality of linear spines comprising a first plurality of linear spines and a second plurality of linear spines that alternate about a central axis;

cutting a discrete cutout at the central spine intersection, the discrete cutout defining a first open area of empty space proximate the central axis, the first open area of empty space approximating a first virtual circle including a first diameter from the central axis, the discrete cutout extending into each of the plurality of linear spines for a first length to define a first open slot defined in each of the first plurality of linear spines and a second open slot defined in each of the second plurality of linear spines, each first open slot and each second open slot being contiguous to a circumference of a second virtual circle greater than the first virtual circle, each first open slot tapering in width from the first open area of empty space towards a proximal portion of the plurality of linear spines, each second open slot comprising a respective aperture that defines a third area of empty space such that each linear spine of the second plurality of linear spines bulges outwardly, in a width direction of each spine of the second plurality of spines, in a region proximate the respective aperture;

inserting each spine of the plurality of linear spines into a lumen of at least one electrode; and fitting ends of the plurality of linear spines to a tubular shaft sized to traverse vasculature such that the central spine intersection is positioned at a distal end of the medical probe and respective spines are movable from a tubular configuration to a bowed configuration.

15. The method according to claim 14, further comprising cutting the plurality of linear spines from a pattern comprising longitudinal and transverse scores.

16. The method according to claim 14, further comprising cutting at least two cutouts at the central spine intersection.

17. The method according to claim 14, further comprising offsetting the at least one electrodes between adjacent spines.

18. The method according to claim 14, wherein each electrode comprises a relief adjacent the lumen to allow a wire to extend adjacent to the lumen.

19. The method according to claim 18, further comprising electrically connecting the wire to the at least one electrodes.

20. The method according to claim 14, further comprising disposing an insulative sleeve over the each of the plurality of linear spines and within the lumen of a respective electrode of the at least one electrode.

* * * * *